United States Patent
Rendon

(10) Patent No.: US 9,339,956 B2
(45) Date of Patent: May 17, 2016

(54) MOLDING THERMOTROPIC LIQUID CRYSTALLINE POLYMERS

(75) Inventor: Stanley Rendon, Eagan, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 880 days.

(21) Appl. No.: 13/516,270

(22) PCT Filed: Dec. 16, 2010

(86) PCT No.: PCT/US2010/060732
§ 371 (c)(1),
(2), (4) Date: Jun. 15, 2012

(87) PCT Pub. No.: WO2011/075569
PCT Pub. Date: Jun. 23, 2011

(65) Prior Publication Data
US 2012/0258284 A1  Oct. 11, 2012

Related U.S. Application Data

(60) Provisional application No. 61/287,799, filed on Dec. 18, 2009, provisional application No. 61/419,049, filed on Dec. 2, 2010.

(51) Int. Cl.
*B29C 45/00* (2006.01)
*B29C 45/77* (2006.01)
(Continued)

(52) U.S. Cl.
CPC ............. *B29C 45/0001* (2013.01); *B29C 45/77* (2013.01); *B29C 2045/0094* (2013.01); *B29K 2105/0079* (2013.01); *B29L 2031/7544* (2013.01); *Y10T 428/24479* (2015.01)

(58) Field of Classification Search
USPC ...................... 264/331.11; 428/156
See application file for complete search history.

(56) References Cited

U.S. PATENT DOCUMENTS 5,151,231 A  9/1992 Lambert
5,262,473 A  11/1993 Cottis
(Continued)

FOREIGN PATENT DOCUMENTS

CN  0662381  7/1995
DE  19856162  6/2000
(Continued)

OTHER PUBLICATIONS

Boles, D. et. al, (2008), Polymer, 49,p. 3541-3553 (cited reference).*
(Continued)

*Primary Examiner* — Benjamin Schiffman
(74) *Attorney, Agent, or Firm* — Gregory D. Allen

(57) ABSTRACT

A method of molding a composition comprising a thermotropic liquid crystalline polymer (TLCP) comprising mesogens; providing a mold having a mold cavity, with a feature cavity (43) comprising a fine feature chamber; heating the composition to form molten composition; filling the fine feature chamber with molten composition moving at a flow velocity that causes flow alignment of at least a portion of the mesogens in the molten TLCP filling the fine feature chamber (49), relative to a flow direction of the moving molten composition; and solidifying the molten composition such that mesogens of at least the solidified TLCP in the fine feature chamber maintain their flow alignment. A molded article comprising a body and a 3-dimensional structural feature protruding out from the body and comprising a fine feature element having a minor dimension, with TLCP mesogens across the minor dimension being in a flow aligned state.

20 Claims, 12 Drawing Sheets

(51) Int. Cl.
B29K 105/00 (2006.01)
B29L 31/00 (2006.01)

(56) References Cited

U.S. PATENT DOCUMENTS

| | | | |
|---|---|---|---|
| 5,456,875 | A | 10/1995 | Lambert |
| 7,317,066 | B2 | 1/2008 | Benicewicz |
| 2002/0155280 | A1 | 10/2002 | Yang |
| 2003/0028154 | A1 | 2/2003 | Ross |
| 2005/0286842 | A1 | 12/2005 | Risch |
| 2007/0200094 | A1 | 8/2007 | Hosoda |
| 2008/0203358 | A1 | 8/2008 | Mizumoto |

FOREIGN PATENT DOCUMENTS

| | | |
|---|---|---|
| EP | 0447726 | 9/1991 |
| EP | 1 222 937 | 7/2002 |
| EP | 1362682 | 11/2003 |
| EP | 1621581 | 2/2006 |
| JP | 9141701 | 6/1997 |
| WO | WO 00-72901 | 12/2000 |
| WO | WO 01-51555 | 7/2001 |
| WO | WO 02-34017 | 4/2002 |
| WO | WO 0234017 A2 * | 4/2002 |
| WO | WO 02-37156 | 5/2002 |
| WO | WO 03-078131 | 9/2003 |
| WO | WO 2004-007590 | 1/2004 |
| WO | WO 2004-065462 | 8/2004 |
| WO | WO 2010-117602 | 10/2010 |
| WO | WO 2012-041337 | 4/2012 |
| WO | WO 2012-074576 | 6/2012 |

OTHER PUBLICATIONS

Rendon, S. et. al, Rheolo. Acta, (2007),46:945-956.*
Fang, J., Polymer Engineering and Science, (2010), 50:1864-1877.*
Nguyen T.N. et. al., Polymer Engineering and Science, (2000), 40 (7), 1643-1654.*
Iam-Choon, Khoo, Liquid Crystal, Second Edition, 2006, $2^{nd}$, p. 1, 6-8.*
R. A. Weiss, ACS Symposium Series, 1989,1-2.*
K.F. Wissbrun, Chemical Engineering Communications, vol. 53 (1-6), p. 149-173.*
Kawasumi, "Functional Liquid Crystalline Polymers", Toyota Central R&D Labs Review, Dec. 1993, vol. 28, No. 4, pp. 13-24.
Boles, "A novel microstream injection molding method for thermotropic liquid crystalline polymers to promote mechanical isotropy: A matrixing microbeam X-ray study", *Polymer*, 49, (2008) pp. 3541-3553.
Burghardt, "Molecular orientation and rheology in sheared lyotropic liquid crystalline polymers", *Macromolecular Chemistry and Physics*, 199, (1998), pp. 471-488.
Gabriele, "How to Process LCP's", *Plastics Technology*, (Apr. 1990), pp. 92-98.
Larson, "Development of Orientation and Texture During Shearing of Liquid-Crystalline Polymer", *Liquid Crystals*, (1992), 12, pp. 751-768.
Rendon, "Orientation dynamics in commercial thermotropic liquid crystalline polymers in transient shear flows", *Rheologica Acta*, 46, (2007), pp. 945-956.
Rendon, "Processing, Structure and Property Relationships in Commercial Thermotropic Liquid Crystalline Polymers", *Northwestern University*, Ph.D. Thesis, (2006), 471 pages.
Wang, "Liquid crystal polymer (LCP) for MEMS: processes and applications", J. Micromech. Microeng, 13, (2003), pp. 628-633.
Zhao, "A new liquid crystalline polymer based processing aid and its effects on micro-molding process", *Journal of Materials Processing Technology*, 168, (2005), pp. 308-315.
International Search Report for PCT/US2010/060732, Mailing Date Mar. 11, 2011, 5 pages.

* cited by examiner

MOLDING THERMOTROPIC LIQUID CRYSTALLINE POLYMERS

CROSS REFERENCE TO RELATED APPLICATIONS

This application is a national stage filing under 35 U.S.C. 371 of PCT/US2010/060732, filed Dec. 16, 2010, which claims priority to U.S. Provisional Application No. 61/287,799, filed Dec. 18, 2009, and U.S. Provisional Application No. 61/419,049, filed Dec. 2, 2010, the disclosures of which are incorporated by reference in their entireties herein.

The present invention pertains to the use of liquid crystalline polymers, in particular to the use of thermotropic liquid crystalline polymers, and more particularly, to molding with thermotropic liquid crystalline polymers and articles molded therefrom.

BACKGROUND

There are a variety of processes and equipment used for molding polymeric materials into molded articles. Injection molding is one type of process widely used to mold many different types of polymeric articles. There are two basic types of injection molding techniques. One type of injection molding technology uses a cold runner system 10, for example, like that shown in FIGS. 1A and 1B. Typically, the cold runner injection molding system 10 relies on a reciprocating screw extruder (not shown) to supply a molten polymeric material into a mold 11 via a nozzle 12 in fluid communication with the mold 11 through a nozzle seat 13. The mold 11 has a first mold half 14 and second mold half 15 that define a mold cavity that includes a sprue passage 16 formed through the first mold half 14, which directs molten polymeric material supplied from the nozzle 12 into a body cavity 17 forming part of the mold cavity. The body cavity 17 includes a runner passage 18 that directs molten polymeric material from the sprue 16 to two part cavities 19 and 20 through separate gate openings 21 and 22, respectively. The gates 21 and 22 determine the flow field of the molten polymeric material injected into the corresponding part cavities 19 and 20. After the molten polymeric material filling the sprue 16 and body cavity 17 has solidified, the mold halves 14 and 15 are separated and the solidified article removed. To facilitate removal of the molded article, a plurality of ejection pins 23 are mounted in the second mold half 15, and used, so as to push the molded article out of the second half 15.

Another type of injection molding technology uses a hot runner molding system. A hot runner injection molding system is similar in construction to a cold runner system except that the sprue and runner cavities are heated so that the molten polymeric material remains molten as it passes through to the part cavities. Thus, in a hot runner system, the molten polymeric material injected into the part cavities is typically the only molten polymeric material solidified and eventually removed from the mold.

Such conventional injection and other molding systems have been used to form a variety of molded articles having a wide range of feature designs and sizes. A variety of different polymeric materials have also been used to mold into articles using such equipment. One polymeric material known to be used in making injection molded articles is thermotropic liquid crystalline polymers (TLCP). On the molecular level, TLCPs are comprised of rigid moieties that form segments in the polymer chains. These rigid moieties are known as "mesogens." TLCPs are known for exhibiting desirable properties, which can include one or more of high impact resistance, low coefficient of thermal expansion, resistance to chemical degradation, low weight, high strength, and high modulus among other properties.

There are limits to the mold feature designs and sizes that can be filled with known polymeric molding materials using conventional molding systems. Therefore, there is a continuing need for molding systems, especially injection molding systems, that are capable of molding articles having even smaller and more intricate design features. The present invention fulfills this need.

SUMMARY OF THE INVENTION

In one aspect of the present invention, a method is provided for injection or otherwise molding an article. The method comprises providing a composition that comprises at least one melt processable or thermotropic liquid crystalline polymer (TLCP), with the TLCP comprising a plurality of mesogens, and providing a mold comprising a mold cavity, with the mold cavity comprising at least one feature cavity, and each feature cavity comprising at least one fine feature chamber. The method further comprises heating the composition so as to form molten composition comprising molten TLCP, and filling the mold cavity with a desired amount of the molten composition. The mold cavity is filled such that the molten composition filling the at least one fine feature chamber is moving at a flow velocity that causes flow alignment of all or at least a substantial portion of the mesogens in the corresponding molten TLCP (i.e., the molten TLCP filling the at least one fine feature chamber) relative to a flow direction of the moving molten composition. The molten composition is solidified such that mesogens of at least the solidified TLCP in the at least one fine feature chamber (i.e., the mesogens in the corresponding at least one fine feature element of the resulting molded article) maintain their flow alignment.

The mold cavity used in this method can further comprise a body cavity, with each feature cavity extending from and being connected with the body cavity. With this embodiment, the step of filling the mold cavity comprises filling the body cavity with a desired amount of the molten composition such that at least a portion of the molten composition filling the body cavity is moving at a first flow velocity that causes flow tumbling of mesogens in the corresponding molten TLCP (i.e., the molten TLCP filling the body cavity). In addition, the flow velocity of the molten composition filling each fine feature chamber is a second flow velocity that is faster than the first flow velocity.

In an another embodiment, the step of filling the mold cavity comprises filling the body cavity with a desired amount of the molten composition such that at least a portion of the molten composition filling the body cavity is moving at a flow velocity that causes flow alignment of mesogens in the molten TLCP filling the body cavity. With this embodiment, the step of solidifying the molten composition can be performed such that the flow alignment of mesogens in the body cavity is maintained or at least reduced. To obtain a flow alignment of mesogens in the body cavity that is at least reduced, the step of solidifying can also comprise solidifying the molten composition filling each fine feature chamber before solidifying the molten composition filling the body cavity, and solidifying the molten composition in the body cavity after the flow alignment of the mesogens in the body cavity has had enough time to be at least reduced. The flow alignment of mesogens in the body cavity can also be at least reduced by solidifying the molten TCLP such that the flow alignment of mesogens in each fine feature chamber and the body cavity are maintained;

re-melting solidified TCLP in the body cavity; and re-solidifying the re-melted TCLP in the body cavity.

In another aspect of the present invention, a molded article is provided that comprises a body and at least one 3-dimensional structural feature integral with and protruding out from the body. Each structural feature comprises at least one or a plurality of fine feature elements, with each fine feature element having a minor dimension. Each structural feature comprises at least one melt processable or thermotropic liquid crystalline polymer (TLCP) having a plurality of mesogens, with at least a portion of the mesogens across the minor dimension being in a flow aligned state (i.e., a state having a relatively anisotropic alignment compared to the alignment resulting from mesogen flow tumbling). The body of this article can be formed using a body cavity in accordance with any of the above methods. The at least one structural feature of this article can also be formed using the at least one feature cavity in accordance with any of the above methods. In addition, the at least one fine feature element of this article can be formed using the at least one fine feature chamber in accordance any of with the above methods.

Because the molten composition is flowing at a velocity that causes flow alignment of mesogens in the molten TLCP, the molten composition is able to fill the at least one fine feature chamber. If not for these mesogens being flow aligned, the molten composition would not be able to adequately fill the at least one fine feature chamber. That is, the at least one fine feature chamber would not be filled with enough of the molten composition to form the corresponding molded fine feature element so as to be suitable for its intended purpose. In addition, the mesogens in the solidified at least one fine feature element are sufficiently flow aligned to provide the at least one fine feature element with the physical properties (e.g., stiffness, flexure strength, or other mechanical properties) needed for its intended purpose.

The terms "comprises" and variations thereof do not have a limiting meaning where these terms appear in the description and claims.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a mold cavity that comprises "a" fine feature chamber group can be interpreted to mean that the mold cavity includes "at least one" or "one or more" fine feature chambers. In addition, the singular forms "a", "an", and "the" encompass embodiments having plural referents, unless the content clearly dictates otherwise.

The term "and/or" means one or all of the listed elements or a combination of any two or more of the listed elements. In addition, the term "or" is generally employed in its sense including "and/or" unless the content clearly dictates otherwise.

The recitation of numerical ranges by endpoints includes all numbers subsumed within that range (e.g. 1 to 5 includes 1, 1.5, 2, 2.75, 3, 3.80, 4, and 5) and any range within that range.

The term "polymer" will be understood to include polymers, copolymers (e.g., polymers formed using two or more different monomers), oligomers and combinations thereof, as well as polymers, oligomers, or copolymers that can be formed in a miscible blend.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF CERTAIN EMBODIMENTS

Figure 1A:
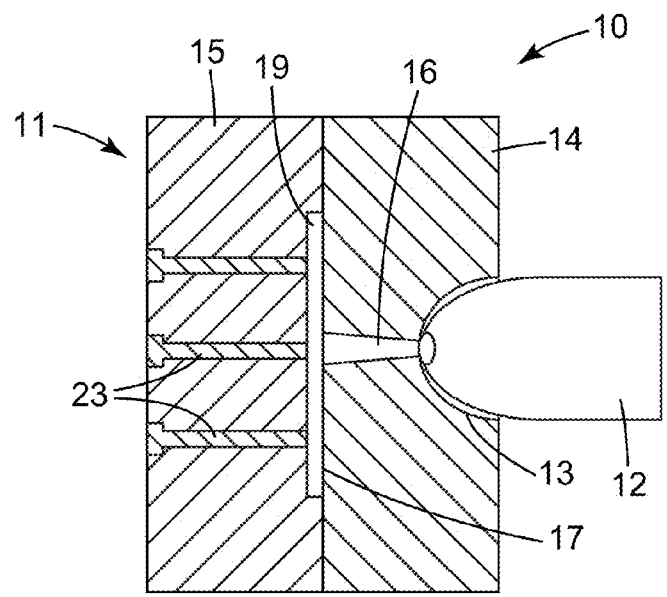
FIG. 1A is a cross sectional side view a mold die for a cold runner injection molding device in accordance with the prior art.
Figure 1B:
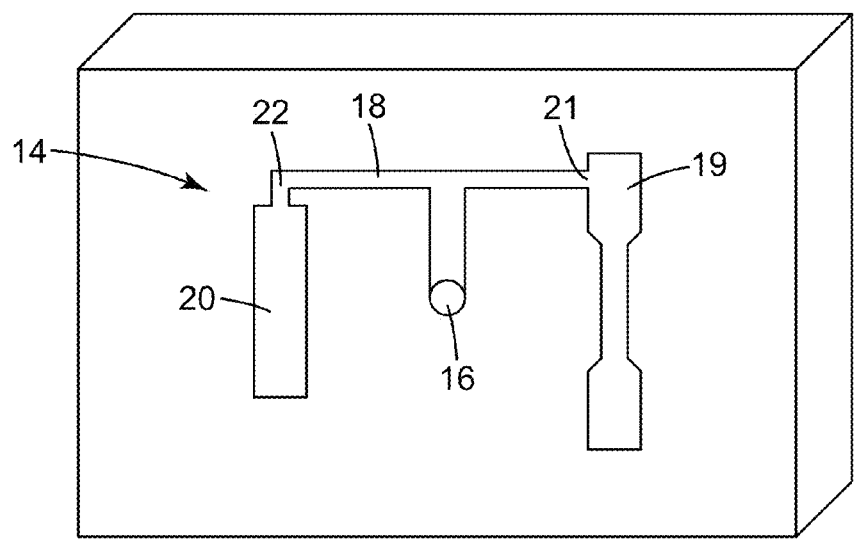
FIG. 1B is a perspective face view showing the mold cavity of half of the mold die of the cold runner injection molding device of FIG. 1A.

In describing preferred embodiments of the invention, specific terminology is used for the sake of clarity. The invention, however, is not intended to be limited to the specific terms so selected, and each term so selected includes all technical equivalents that operate similarly. The molding process of the present invention can offer one or more advantages including one or more of the following advantages: the ability to tailor macroscopic properties of a molded article by selectively controlling the extent to which mesogens in the TLCP flow align and/or flow tumble during molding, the ability to reliably reproduce the shape of the article mold cavity in the resulting molded article, the ability to produce article features of submicrometer dimensions, the ability to produce fine article features having anisotropic physical properties, and/or the ability to produce fine article features having balanced physical mesoscopic properties.

Method Embodiment 1

In one method of molding (e.g., injection molding) an article, according to the present invention, a composition is provided that consists of, consists essentially of, comprises, is formed entirely of, is formed substantially of (i.e., at least about 50% and preferably at least about 60%), or is formed at least in part with at least one thermotropic, or otherwise melt processable, liquid crystalline polymer (TLCP). The TLCP comprises a plurality of mesogenic groups or molecular mesogens. Such TLCP mesogens are often defined as anisotropic molecular moieties incorporated into the polymeric backbone architecture of the TLCP. Suitable TLCPs can include, for example, copolymers consisting of aromatic aliphatics, aromatic polyesters, polyazomethines, polyamides, and combinations thereof.

The mold used in this molding process includes a mold cavity comprising one or a plurality of feature cavities (e.g., micro-needle shaped cavities). Each feature cavity comprises one or more fine feature chambers connected so as to be in fluid communication with the feature cavity. The composition is heated so as to form molten composition comprising molten TLCP. The mold cavity is filled with a desired amount of the molten composition such that the molten composition filling each feature cavity, or at least each fine feature chamber, is moving at a flow velocity that is fast enough to cause flow alignment of all or at least a substantial amount of the TLCP mesogens in the molten TLCP filling each feature cavity or at least filling each fine feature chamber. These TLCP mesogens are flow aligned relative to the flow direction of the molten composition as the molten composition fills each feature cavity or at least each fine feature chamber. The mold cavity can be filled, for example, by forcing molten composition into the mold cavity using a screw or other extruder, a plunger or piston arrangement, or any other suitable technique capable of filling the mold cavity. After the one or more fine feature chambers are filled to a desired degree with molten composition, the molten composition is solidified by being cooled (e.g., by cooling the mold), or at least by being allowed to cool (e.g., by allowing the mold to cool). The molten composition in each feature cavity, or at least each fine feature chamber, can be the first to solidify. The molten composition is solidified such that the flow alignment of all or at least a substantial amount (percentage) of the TLCP mesogens in at least each fine feature chamber is completely or at least substantially maintained. A substantial percentage of the TLCP mesogens are considered flow aligned when the portions of the molded article formed in at least the fine feature chambers exhibit the degree of unidirectional or anisotropic physical properties desired for the chosen application.

In commercially relevant TLCPs, mesogens constitute the most fundamental unit of the liquid crystal polymer that induces structural order in an arrangement known as a "nematic," which is characterized by mesophase units that display long range orientational order, but only short range packing or positional order. The alignment of the mesogens along an average orientation direction (or vector) defined as the "director" can be characterized by a molecular anisotropy factor (from now on referred to as the "anisotropy factor") which ranges from 0 for a random distribution of mesogen molecular orientations (i.e., isotropic) and 1 for perfect molecular alignment.

As used herein, the term "molten TLCP" refers not only to all of a TLCP being in a molten state (i.e., where its mesogens can flow tumble) but also to a TLCP having its mesogens in the form of solid oriented crystalline regions (e.g., where the mesogens are flow aligned) with the remainder of the TLCP being molten (e.g., being in the form of one or a plurality of fluid amorphous regions).

As used herein, the term "flow aligned" refers to the TLCP mesogens exhibiting an anisotropy factor in the range of from at least about 0.4 up to 1.0, preferably from at least about 0.5 up to but less than 1.0, and more preferably from about 0.6 to less than 1.0, relative to the flow direction.

In accordance with the present invention, the molten composition filling each fine feature chamber is considered to have a substantial portion of its TLCP mesogens flow aligned, depending on the application, when at least about 30% up to 100%, 35% up to 100%, 40% up to 100%, 45% up to 100%, 50% up to 100%, 55% up to 100%, 60% up to 100%, 65% up to 100%, 70% up to 100%, 75% up to 100%, 80% up to 100%, 85% up to 100%, 90% up to 100%, or 95% up to 100% of the TLCP mesogens filling the minor dimension of each fine feature chamber are flow aligned. Such minor dimensions in the fine feature chamber can be, e.g., the portion of the fine feature chamber that forms the thickness of a wall, diameter of a needle tip, etc. Correspondingly, the portion of the molded article formed by each fine feature chamber is considered to have a substantial portion of aligned TLCP mesogens, when at least about 30% up to 100%, 35% up to 100%, 40% up to 100%, 45% up to 100%, 50% up to 100%, 55% up to 100%, 60% up to 100%, 65% up to 100%, 70% up to 100%, 75% up to 100%, 80% up to 100%, 85% up to 100%, 90% up to 100%, or 95% up to 100% of the TLCP mesogens across the minor dimension of the each such fine feature (e.g., thickness of a wall, diameter of a needle tip, etc.) are flow aligned. For some applications (e.g., the tip of a microneedle), it can be desirable for a maximum of about 25% of the TLCP mesogens across the minor dimension of each fine feature chamber to be flow tumbled (i.e., for a maximum of about 25% of the minor dimension of the corresponding portion of the molded article to be isotropic). For other applications, higher amounts of flow tumbled TLCP mesogens in each fine feature chamber may be tolerable. For other applications, even a lower maximum of flow tumbled TLCP mesogens in each fine feature chamber may be necessary.

TLCP mesogens will quickly begin to rotate—from a flow aligned state—at molding temperatures where the TLCP is molten. As a result, the molten TLCP in at least the fine feature chamber(s) should be solidified rapidly, after the fine feature chamber(s) is filled, to ensure that a substantial amount of the flow aligned mesogens remain flow aligned in the portion(s) of the molded article formed by the fine feature chamber(s). The dimensions of each fine feature chamber and of the portion of the mold defining the fine feature chamber(s), as well as the material(s) used to form that portion of the mold can affect the cooling rate of the molten TLCP in the fine feature chamber(s). For example, the smaller the minor dimension of the fine feature chamber (e.g., the dimension defining the thickness of a wall feature of a molded article), the faster the cooling rate, because there is less molten TLCP to be solidified. In addition, if the mold is made of a less thermally conductive material such as, e.g., stainless steel versus a more thermally conductive material such as, e.g., a copper alloy, larger or bulkier mold designs would result in a slower cooling rate, because a mold material having a lower thermal conductivity would conduct heat away from the molten TLCP at a slower rate. This cooling rate will determine whether a suitable amount of the TLCP mesogens will remain flow aligned to provide the physical properties desired in the solidified molded article.

The flow aligned TLCP mesogens can be found throughout the molded element of the article formed by each feature cavity or at least formed by each fine feature chamber. Alternatively, the flow aligned TLCP mesogens of the molded element, formed by each feature cavity or at least formed by each fine feature chamber, can be found in an outer zone or thickness (e.g., a skin) that encases a core of the molten composition that contains TLCP mesogens that are not flow aligned, as compared to the outer zone or thickness, (e.g., that are mostly or completely flow tumbled or otherwise isotropic). Such an outer zone or thickness of flow aligned TLCP mesogens can be formed under three possible conditions: (1) when the minor dimension is too large to allow for a sufficiently high flow rate across the entire minor dimension, (2) when only the outer portion is cooled fast enough to solidify the mesogens in a flow aligned state, or (3) both (1) and (2). When the minor dimension is small enough and the cooling rate of the molten TLCP fast enough, all the mesogens in the molten TLCP across the entire minor dimension can be in a flow aligned state and remain flow aligned when the molten TLCP is solidified.

Figure 4A:
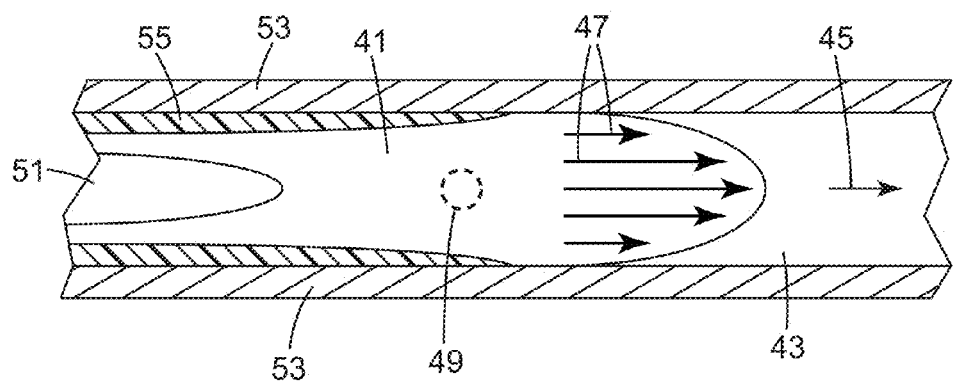
FIG. 4A is a cross sectional plan view of a feature cavity of a mold cavity being filled with a molten TLCP so as to flow align mesogens in the molten TLCP.
Figure 4B:
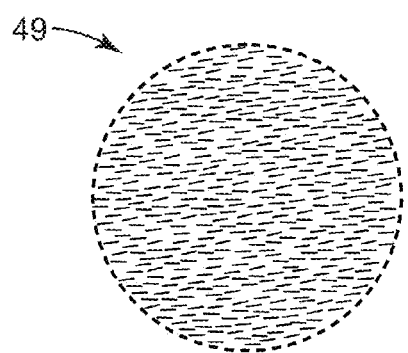
FIG. 4B is an enlarged view of a portion of FIG. 4A.

Referring to FIGS. 4A and 4B, all or at least a substantial outer zone or thickness 41 of a molten TLCP composition filling a feature cavity 43 in accordance with the present invention is moving along a flow direction 45 at a flow velocity (represented by the shear flow velocity vectors 47) that is fast enough to transition the TLCP mesogens from a flow tumbling state to a flow aligning state (see the enlarged area 49). The cavity 41 is designed for molding a thin wall section of the article being molded. The outer thickness encases a core 51 of the molten composition that contains TLCP mesogens that are not flow aligned, as compared to the mesogens in the outer zone 41 (e.g., the mesogens in the core 51 can be mostly or completely flow tumbled or otherwise isotropic). A portion of the outer thickness 41 in contact with the walls 53 of the cavity 43 typically solidifies upon contact to form a skin 55 having mesogens in a flow aligned state. The velocity vectors 47 are generally parallel to the direction of flow 45 of the molten composition.

Figure 4C:
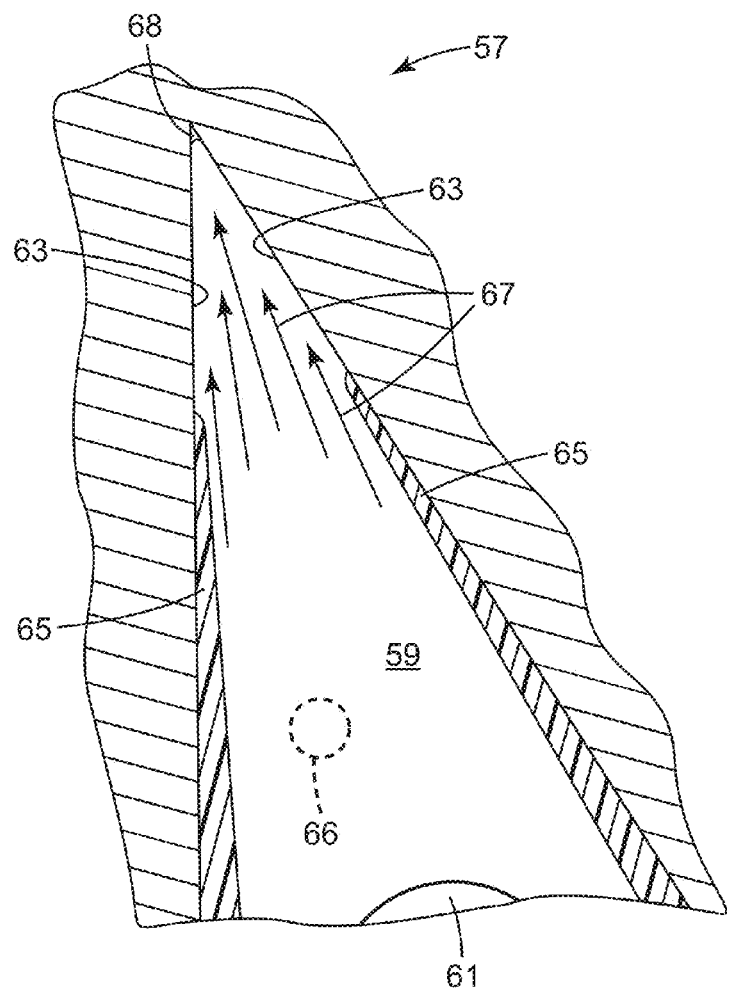
FIG. 4C is a cross sectional plan view of a fine feature chamber of a mold cavity being filled with a molten TLCP so as to flow align mesogens in the molten TLCP.
Figure 4D:
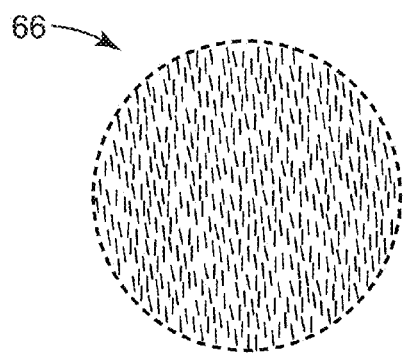
FIG. 4D is an enlarged view of a portion of FIG. 4C.

Referring to FIGS. 4C and 4D, the flow aligned state of the TLCP mesogens in the molten composition allows for injection of the molten composition into very confined spatial regions of the mold cavity such as a fine feature chamber (e.g., the tip of a microneedle 57). All or almost the entire volume of chamber 57 is filled with a molten TLCP composition 59 having flow aligned mesogens (see the enlarged area 66). As the molten composition 59 fills the chamber 57, the flow aligned mesogens follow directions of flow (represented by arrows 67) that converge at the apex of the needle tip. With such convergence, depending on the dimensions of the chamber 57, the flowing mesogens tend to interfere with one another and can prevent complete filling of the chamber 57, and leaving an empty space 68. The flow aligned composition 59 may include a minor core 61 containing TLCP mesogens that are not flow aligned, as compared to the mesogens in the composition 59 (e.g., the mesogens in the core 61 can be mostly or completely flow tumbled or otherwise isotropic). A portion of the flow aligned composition 59 in contact with the walls 63 of the cavity 57 typically solidifies upon contact to form a skin 65 having mesogens in a comparable flow aligned state.

Method Embodiment 2

A version of the above described method embodiment 1, wherein the provided mold cavity further comprises a body cavity, with each feature cavity extending from and being connected so as to be in fluid communication with the body cavity such that the molten composition can flow from the body cavity into each feature cavity. In this method embodiment 2, the step of filling the mold cavity comprises filling the body cavity with a desired amount of the molten composition, where all or at least a substantial portion of the molten composition used to fill the body cavity is moved at a first flow velocity, and the first flow velocity causes flow tumbling of all, a substantial amount of, or at least some of the mesogens in the molten TLCP filling the body cavity. Typically, a core or central region of the molten composition filling the body cavity is moving at a first flow velocity and is flow tumbling. This core forms a substantial portion of the molten composition filling the body cavity. For at least some applications, the core forms such a substantial portion when it is formed by a volume of the molten composition in the range of from about 65% to about 99%. The velocity required to cause TLCP mesogens to transition from being flow tumbled to flow aligned can depend on a number of factors including, for example, the density, flowability, and viscosity of the molten composition, which can be temperature dependant, and the volume and cross sectional dimensions (i.e., geometry) of the body cavity.

Also in this method embodiment 2, after all or at least a substantial portion of the body cavity is filled with molten composition, the one or more feature cavities connected to the body cavity are filled, including the one or more fine feature chambers. The flow velocity of the molten composition filling each feature cavity, or at least filling each fine feature chamber, is increased to a second or increased flow velocity that is faster than the first flow velocity. This second flow velocity is fast enough to cause the flow alignment of all or at least a substantial amount of the mesogens in the molten TLCP filling each feature cavity or at least filling each fine feature chamber. The TLCP mesogens are flow aligned relative to a flow direction of the molten composition as the molten composition fills each feature cavity or at least each fine feature chamber. After all of the fine feature chambers are filled to a desired degree with molten composition, the molten composition is cooled or at least allowed to cool (e.g., by allowing the mold to cool) so as to solidify the molten composition in the mold cavity (i.e., in the body cavity, each feature cavity and each fine feature chamber).

Regardless of whether the mesogens in the body cavity are solidified in a flow tumbled or flow aligned state, the body cavity can be used to form a body portion of the article being molded, or alternatively, the body cavity can be used to form a structure that does not form a portion of the molded article (e.g., the body cavity can be designed to form a sprue or runner). When it forms a portion of the molded article, the body cavity can be designed to form, for example, a film-shaped, plate-shaped, hub-shaped, or other shaped body portion of the article. When it does not form part of the molded article, the body cavity can be designed to form, for example, a sprue or runner that may be scrapped or recycled. The body cavity can be in the form of a manifold body cavity that joins together a plurality of feature cavities. The solidified composition formed in such a manifold body cavity may not form part of the article being molded. As a result, it may be desirable to scrap or recycle the solidified composition in such a manifold body cavity. Similarly, the feature cavity can be in the form of a manifold feature cavity that joins together a plurality of fine feature chambers and is in communication with the body cavity. The solidified composition formed in such a manifold feature cavity may not form part of the article being molded. As a result, it may be desirable to scrap or recycle the solidified composition in such a manifold feature cavity.

Each fine feature chamber can define at least one leading portion—or all—of the corresponding feature cavity. Each fine feature chamber can also form one or more features that are very fine. As used herein, a feature that is "very fine" is a feature that has at least one minor dimension (e.g., a wall feature having a thickness) that is less than or equal to about 20 micrometers (microns). In order for the molten composition to fill such a fine feature chamber of the mold and, after cooling, form the resulting fine feature of a molded article, according to the present invention, the molten TLCP should exhibit a flow tumbling parameter of greater than 1 (i.e., $|\lambda|>1$), and the mesogens in the molten TLCP used to form the fine feature should be aligned so as to exhibit an anisotropy factor of greater than or equal to (i.e., at least) about 0.25 and preferably greater than or equal to about 0.5).

Such substantial mesogen alignment (i.e., nematic alignment) in the fine feature of the molded article can allow the fine feature to exhibit mechanical properties that would otherwise be inadequate to perform the desired function or application of the molded article. For example, to be stiff enough to function as a micro-needle that can penetrate human skin by applying only hand pressure, at least the leading end or tip of such a micro-needle feature (e.g., at least about 0.1% to about 2% by volume of the micro-needle from its tip back toward its base) needs to be made with TLCP material having mesogens that exhibit substantial nematic alignment so as to be coaxial (i.e. substantially parallel) with the longitudinal axis of the micro-needle (i.e., so as to exhibit an anisotropy factor of at least about 0.4, and preferably at least about 0.5).

As used herein, the term "flow tumbling" refers to the unbalanced hydrodynamic torques in shear that promote continuous rotation of the nematic director about the "vorticity axis of flow" of the molecular TLCP mesogens during bulk flow of the molten TLCP filling a desired mold cavity. Therefore, statements that solidified TLCP mesogens are in a "flow tumbled state" refers to the TLCP mesogens having been solidified while in a flow tumbled state (i.e., after being subjected to flow tumbling).

It can be important for the molten TLCP to exhibit flow tumbling before filling each feature cavity, or at least before filling each fine feature chamber, in order to maintain a high enough defect density in the polymer phase (i.e., the polymeric backbone in which the mesogens are incorporated) of the molten composition to promote balanced mechanical properties (e.g., to ensure a balance in mesoscopic properties) in the portion of the molded article formed in the body cavity. The flow alignment of the TLCP mesogens, especially if there is exclusive flow alignment, can lead to very high flow-induced anisotropy factors, which can result in highly unidirectional mechanical properties in the final article being formed. For some applications, highly unidirectional mechanical properties can be undesirable in the portion of the molded article formed in the body cavity (e.g., micro-electronic sensors, Dual In-line Memory Module (DIMM) connectors, sockets, LED housings, micro-gears, etc). For other applications, such highly unidirectional mechanical properties in the body portion of the molded article may be desirable (e.g., solid and hollow microneedle arrays, micro-fluidic mixers, surgical device components, etc).

When it is not necessary to have balanced mechanical properties in the body cavity (e.g., when the body cavity doesn't form part of the finished article and is to be scrapped or recycled), it can be unnecessary or may be even undesirable for the molten composition to flow tumble in the body cavity. Such a body cavity could form, for example, runner or sprue cavity portions of the mold cavity. Flow tumbling of the TLCP mesogens in such a body cavity can be restricted by the geometry and dimensions of the body cavity (e.g., a cold runner or sprue cavity). By forcing the molten composition to pass from an opening having a large cross sectional area (where flow tumbling occurs) and through a smaller opening (where flow alignment occurs), the molten composition can exhibit a rapid transition from a relaxed state, where its mesogens have an equilibrium flow tumbling character (e.g. while the composition is molten in a heated extrusion barrel), to a flow aligned state. For example, the molten composition could pass from the relatively large opening inside of an extrusion barrel and through the relatively small orifice in a nozzle leading from the extrusion barrel directly into such a disposable body cavity (e.g., a cold sprue or runner cavity).

Preferably, the first flow velocity of the molten composition is not increased to the second flow velocity until the body cavity is completely or at least substantially filled with the molten composition. The body cavity is considered substantially filled with the molten composition, when one or more of the feature cavities or at least of the fine feature chambers are about to fill or begin to fill with the molten composition. It can be desirable for the first flow velocity to be in the range of from about 0.0 inches/second (millimeters/second or mm/s) up to about 4 inches/second (108 mm/s). It can be preferable for the first flow velocity to be in the range of from about 0.25 inches/second (6.35 millimeters/second or mm/s) up to about 3 inches/second (76.2 mm/s).

The flow velocity of the molten composition filling the feature cavities and/or the fine feature chambers can be increased, e.g., by increasing the injection pressure or otherwise applied pressure exerted against the molten composition inside and entering the mold cavity. Alternatively or additionally, the increased flow velocity can be obtained by designing the mold cavity geometry such that the flow velocity of the molten composition increases as it enters the feature cavity and/or the fine feature chamber. For example, reducing the minor dimension or otherwise restricting the cross section of the feature cavity and/or fine feature chamber, as applicable, compared to that of the body cavity can facilitate the desired higher flow velocity of the molten composition entering each feature cavity and/or fine feature chamber. It can also be helpful for each feature cavity or at least each fine feature chamber to have a smaller volume than the body cavity, and preferably a considerably smaller volume thereof. Accordingly, the increased pressure applied to the molten composition is maintained until each fine feature chamber is completely or at least substantially filled with the desired amount of molten composition and/or the molten composition in each fine feature chamber has solidified to form the fine feature.

All of the molten composition, or at least a substantial outer zone or thickness of the molten composition, filling each feature cavity or at least each fine feature chamber is moving at the second flow velocity. For some applications, this outer thickness can be substantial when it is a skin region formed using in the range of from about 5% to about 20% by volume of the molten composition filling each feature cavity or at least filling each fine feature chamber. The second flow velocity is preferably maintained until the one or plurality of fine feature chambers are substantially or completely filled with the molten composition. To ensure a transition from a flow tumbling state to a flow aligned state, it can be desirable for the molten composition to experience a rapid increase in velocity, from the first flow velocity to the second flow velocity, that is greater than or equal to about 3 inches/second (76.2 mm/s) is desired.

Method Embodiment 3

Another version of the above described method embodiment 1, wherein the provided mold cavity further comprises a body cavity, with each feature cavity extending from and being connected in fluid communication with the body cavity, and the step of filling the mold cavity comprises filling the body cavity with a desired amount of the molten composition such that all or at least a substantial portion of the molten composition filling the body cavity is moving at a flow velocity that causes complete or at least substantial flow alignment of the mesogens in the molten TLCP filling the body cavity.

Method Embodiment 4

A version of the above described method embodiment 3, wherein the method further comprises: solidifying the molten composition such that the flow alignment of mesogens in the body cavity is completely eliminated, substantially eliminated or at least significantly reduced. The flow alignment of TLCP mesogens in the body cavity is considered significantly reduced, when the solidified composition in the body cavity is more flexible than the solidified composition in the fine feature chamber.

Method Embodiment 5

A version of the method embodiment 4, wherein the solidifying step comprises solidifying the molten composition filling each fine feature chamber before solidifying the molten composition filling the body cavity, and the molten composition in the body cavity is solidified after the flow alignment of the mesogens in the body cavity has had enough time to be completely eliminated, substantially eliminated or at least significantly reduced. For some applications, at least about 500 milliseconds is enough time for the flow alignment of the mesogens in the body cavity to be significantly reduced, with no applied load.

Method Embodiment 6

Another version of the method embodiment 3, wherein the method further comprises: solidifying the molten composition such that the flow alignment of mesogens in the body cavity is completely or at least substantially maintained.

Method Embodiment 7

An additional version of the method embodiment 3, wherein the solidifying step comprises solidifying the molten TCLP such that the flow alignment of mesogens in each feature cavity and in the body cavity are completely or at least substantially maintained. This flow alignment of mesogens can be so maintained by solidifying the TCLP in each feature cavity and in the body cavity at exactly or substantially the same time. In this version, the method further comprises: re-melting all or at least a portion of the solidified TCLP in the body cavity, and re-solidifying the re-melted TCLP in the body cavity. In this way the flow alignment of mesogens in the body cavity is completely eliminated, substantially eliminated, or significantly reduced or at least reduced somewhat.

Method Embodiment 8

A version of any one of the method embodiments 2 to 7, wherein the body cavity corresponds to a body portion of the article being molded.

Method Embodiment 9

Another version of any one of the method embodiments 2 to 7, wherein the body cavity functions as a runner or sprue for supplying molten TCLP to the at least one feature cavity, and the molten TCLP solidified in the body cavity does not form a portion of the article being molded.

Method Embodiment 10

A version of the method embodiment 2, wherein the first flow velocity of the molten composition filling the body cavity is less than or equal to about 108 millimeters per second (mm/s) and preferably in the range from about 6.35 mm/s to about 76.2 mm/s.

Method Embodiment 11

A version of any one of the method embodiments 3 to 7, wherein the flow velocity of the molten composition filling the body cavity is at least about 76.2 mm/s and preferably in the range from about 101.6 mm/s to about 165 mm/s.

Method Embodiment 12

A version of any one of the method embodiments 1 to 11, wherein the flow velocity of the molten composition filling the at least one fine feature chamber is at least about 51 mm/s and preferably in the range from about 51 mm/s to about 127 mm/s.

Method Embodiment 13

A version of any one of the method embodiments 1 to 12, wherein the TLCP is chosen from a group of polymers and copolymers consisting of aromatic aliphatics, aromatic polyesters, polyazomethines, polyamides, and combinations thereof.

Method Embodiment 14

A version of any one of the method embodiments 1 to 13, wherein the mold cavity comprises a plurality of feature cavities, with each feature cavity comprising at least one fine feature chamber connected so as to be in fluid communication therewith.

Method Embodiment 15

A version of any one of the method embodiments 1 to 14, wherein each feature cavity comprises a plurality of fine feature chambers.

Method Embodiment 16

A version of any one of the method embodiments 1 to 15, wherein the at least one fine feature chamber has a minor feature dimension (e.g., thickness) of greater than or equal to about 90 nanometers (nm), or preferably in the range of from about 100 nm up to and including about 20 microns.

Method Embodiment 17

A version of any one of the method embodiments 1 to 16, wherein each fine feature chamber defines a leading portion of the corresponding feature cavity.

Method Embodiment 18

A version of any one of the method embodiments 1 to 16, wherein each feature cavity is defined entirely by its corresponding at least one fine feature chamber.

Method Embodiment 19

A version of any one of the method embodiments 1 to 16, wherein the molten composition is kept at exactly, at least substantially, or about the same temperature until the molten composition or at least the molten TLCP is solidified. For example, it can be desirable for the molten composition to be kept to within plus or minus 50° C. of the melting point of the TLCP being used until the molten composition or at least the molten TLCP is solidified.

Method Embodiment 20

A version of any one of the method embodiments 1 to 19, wherein the molten composition is at a temperature within the range of from about 450° F. (232° C.) up to and including about 800° F. (427° C.).

Method Embodiment 21

A version of any one of the method embodiments 1 to 20, wherein at least the mold cavity is kept at exactly, at least substantially, or about the same temperature until the molten composition is solidified. For example, it can be desirable for at least the mold cavity to be kept approximately within 50° C. of the melting point of the TLCP being used until the molten composition is solidified. Preferably, the mold cavity is kept at a temperature below the heat distortion temperature of the TLCP (e.g., mold cavity temperatures in the range of from about 40° C. up to and including 150° C.). The "heat distortion" temperature of the TLCP refers to the temperature below which the TLCP will not plastically deform under a specified load. For example, the heat distortion temperature can be the temperature below which the TLCP will not flow under applied injection molding pressures. It may also be the temperature below which the TLCP will not flow under other applied external forces.

Method Embodiment 22

A version of any one of the method embodiments 1 to 20, wherein at least each fine feature chamber is kept at exactly, at least substantially, or about the same temperature during the solidifying of the molten composition in the at least one fine feature chamber. For example, it can be desirable to keep at least each fine feature chamber to within plus or minus 30° C. of the melting point of the TLCP being used during the solidifying of the molten composition in the at least one fine feature chamber.

Method Embodiment 23

A version of any one of the method embodiments 1 to 22, wherein each filling step is performed by extruding molten composition into the mold cavity. In other words, the mold cavity can be filled with the desired amount of the molten composition by extruding molten composition into the mold cavity.

Method Embodiment 24

A version of the method embodiment 2, wherein the difference between the first flow velocity and the second flow velocity is at least about 0.5 inches/second (12.7 mm/s), and preferably in the range from about 1.0 inch/second (25.4 mm/s) to about 5.0 in/s (127 mm/s).

Method Embodiment 25

A version of any one of the method embodiments 1 to 24, wherein the time between melting the composition and completely, at least substantially, or about filling the mold cavity with molten composition is less than or equal to about 5.00 minutes. It can be preferable for the mold cavity to be so filled in less than or equal to about 4.5, 4.0, 3.5, 3.0, 2.5, 2.0, 1.5, 1.0, 0.5, 0.45, 0.40, 0.35, 0.30, 0.25, 0.20, 0.15, 0.10, or 0.05 minutes.

Method Embodiment 26

A version of any one of the method embodiments 1 to 24, wherein the time it takes to melt the composition; completely, at least substantially, or about fill the mold cavity with the molten composition; and solidify the molten composition in the mold cavity is in total less than or equal to about 5.00 minutes. It can be preferable for this time to be in the range from about 3 seconds up to about 5 minutes.

Method Embodiment 27

A version of any one of the method embodiments 1 to 26, wherein the molecular mesogens of the TLCP solidified in the at least one fine feature chamber are molecularly aligned, relative to the flow direction of the moving molten composition filling the at least one fine feature chamber, by an anisotropy factor in the range of from greater than 0.4 up to 1.0. Depending on the application, desirable results can be obtained when at least about 30%, 35%, 40%, 45%, 50%, 55%, 60%, 65%, 70%, 75%, 80%, 85%, 90%, 95%, or 100% of the TLCP molecular mesogens in each fine feature chamber are molecularly aligned, as evidenced by an anisotropy factor in the range of from at least about 0.5 up to but less than 1.0, and preferably by an anisotropy factor in the range from about 0.6 up to but less than 1.0.

Method Embodiment 28

A version of any one of the method embodiments 1 to 27, wherein the solidification of the molten composition in each fine feature chamber occurs within less than about 5, 4, 3, 2, 1, 0.9, 0.8, 0.7, 0.6 or 0.5 seconds, after the fine feature chamber is filled with molten composition, depending on the application. After about 5 seconds or more, the flow aligned mesogens have relaxed so much that they are not sufficiently aligned to provide the improved physical properties sought to be obtained by using TLCPs with aligned mesogens.

Method Embodiment 29

A version of any one of the method embodiments 1 to 28, wherein the provided mold comprises a plurality of plates having opposite major surfaces. The plates are designed so as to define each feature cavity or at least each fine feature chamber. At least one or both of the major surfaces of each plate is in contact with a major surface of another of the plates such that gas entrapped in at least the fine feature chambers, and preferably at least the feature cavities, can vent or otherwise escape by passing between the plates and out of the mold, during the filling of the mold cavity. Such a mold is disclosed, for example, in U.S. Provisional Patent Application No. 61/168,268, which is incorporated herein by reference in its entirety. It can be desirable for the plates to define at least a portion of the body cavity. It may be desirable for all of the body cavity formed in one mold half to be defined by such plates. It may also be desirable for such plates to be used to define the entire mold cavity defined by one mold half, the other mold half, or both mold halves.

Method Embodiment 30

A version of the method embodiment 29, wherein each feature cavity or at least each fine feature chamber is vented by submicrometer spacing between the plurality of plates.

Typically when molding articles, venting of the mold cavity is required. Venting of air during the filling of the mold cavity allows displaced air to exit the cavity, thus allowing for more uniform filling of the mold cavity with the molten composition. Typically, a mold comprises two mold halves that mate together to form the mold cavity. The venting of such mold halves is often provided by primary and secondary vents or exit pathways. Such primary and secondary vents can be provided by about 10 μm and about 100 μm deep channels, respectively. The primary and the secondary vents are cut into the major surface of the first mold half of the mold to direct air away from the cavity. The primary vent ensures a path for air to escape while also prohibiting the molten polymeric material from entering because of the large viscosity difference compared to air. The secondary vent ensures that the air being evacuated can freely flow out through the parting line of the mold half. Venting may also be achieved through the ejection pins used to remove the resulting molded article from the mold. While these primary and secondary vents help ensure rough evacuation of the air for the macroscopic portion of the cavity, they do not help mitigate short filling of the respective cavities, resulting in incomplete fill of the cavity and the resulting molded article not having features that as closely match those of the corresponding mold cavity.

Venting of one or more or all of the various mold cavities can be provided by submicrometer spacing between the plurality of plates. In the stacked laminate, each respective plate's first major surface and second major surface can be unpolished, leaving a slight roughness to each major surface. The plates forming a stacked laminate can comprise a surface roughness over the entire area, substantially the entire area, or selected areas of each plate's first and second major surfaces. Such surface roughness can be less than or equal to 30 RMS (root mean square) pinch (0.762 RMS μm), less than or equal to 20 RMS pinch (0.508 RMS μm), less than or equal to 10 RMS pinch (0.254 RMS μm) or even less than or equal to 4 RMS pinch (0.102 RMS μm). Although the plurality of plates are in intimate contact with one another, the submicrometer roughness of the contacting plate surfaces enables the air forced to leave the applicable mold cavity (e.g., body cavity, feature cavity and/or fine feature chamber) to be vented in between adjacent plates. Further, because the venting is in the submicrometer range, the molten composition remains contained within the mold cavity due to its much higher viscosity relative to the evacuated air. The submicrometer venting allows for full air evacuation within the stacked laminate mold, which in turn allows for thermoplastic injection molding at mold temperatures 10 to 20° F. cooler, reduced injection pressures 25 to 30%, shorter cycle times (20 to 30 sec faster), and increases in both the mold and micro-tooling life. The submicrometer venting can also enable finer feature sizes (e.g., sharper needle tip sizes) in the resulting molded article. For example, microneedles made according to the present invention can have a tip diameter of 20, 10, 7, 5, 2, 1, 0.8, or even 0.5 μm or less.

Figure 5:
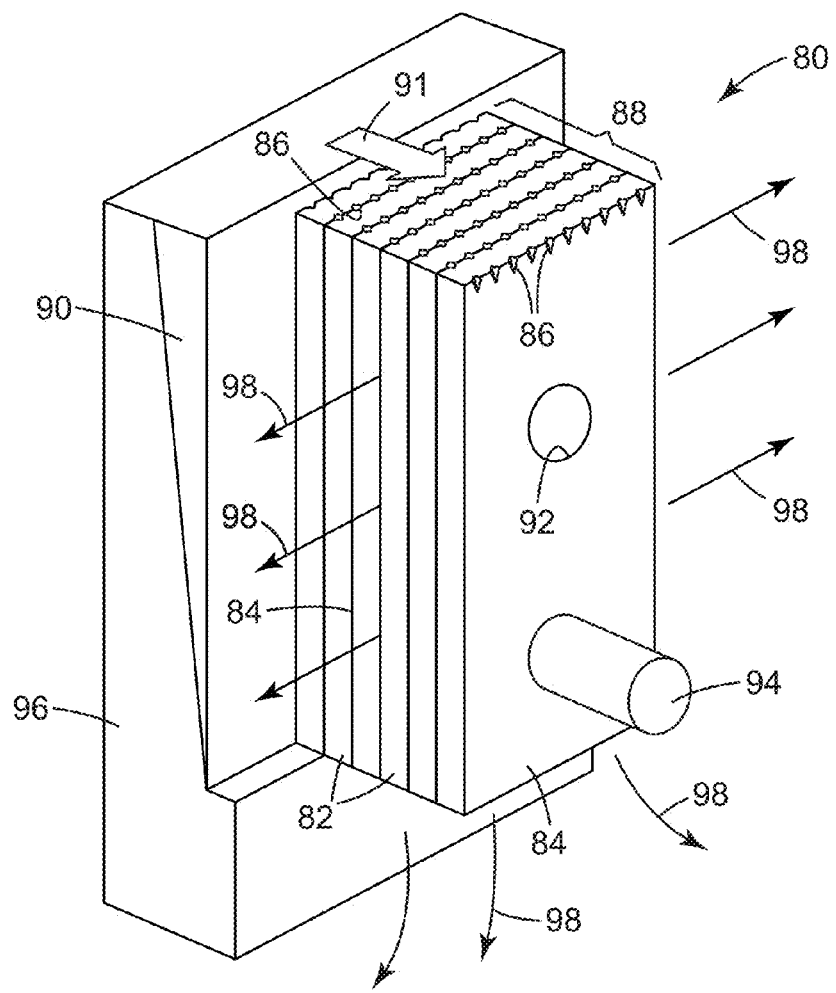
FIG. 5 is a perspective view of a stacked laminate of mold plates that allow air to vent out of its feature cavities between the mold half plates.

Referring to FIG. 5, an example of a stacked laminate mold half 80 comprises a plurality of plates 82 having opposite major surfaces 84 formed with grooves 86 that define feature cavities. The exposed ends 88 of the plates together define at least part of a face of the body cavity formed by the mold that includes mold half 80. The plates 82, which start out loosely stacked, are stacked together tightly, e.g., by use of a wedge block 90 in the direction indicated by arrow 91 so as to make contact between opposing major surfaces 84 of adjoining plates 82. Two holes 92 machined through the major surfaces 84 of each plate 82 are filled with pins 94 that help keep the plates 82 aligned and together, which facilitates using the wedge block 90. The plates 82 can be made of any suitable mold material such as, for example, steel (e.g., spring steel, H13, S7, 420 stainless steel, high carbon steel, etc.). Except for their exposed end surfaces 88, the remainder of each plate 82 is typically hidden within the mold half 80. In this example, the plates 82 are mounted within a block 96 that forms part of the mold half 80. It is desirable for the block 96 to be made of heat conductive metal (e.g., Beryllium Copper Moldstar® from Moldmax® Thermal Management Solutions, Southfield Mich.), which is used to maintain appropriate temperature control surrounding the mold cavity and provide good heat transfer for cooling of the molded article. For this example, portions of the block 96 have been removed to more readily see the sides of the stacked laminate of plates 82 and the paths followed by the air vented out from between the plates 82. The vented air pathways are illustrated by arrows 98.

Each of the above described exemplary methods can be used to form a variety of different molded articles. In addition, the filling of each feature cavity with molten composition can result in a structural feature that is hollow (e.g., a hollow needle), a structural feature that is solid (e.g., a solid needle or pin), or a combination of both. Hollow articles, like hollow needles, can be made using a mold such as that disclosed, for example, in U.S. Provisional Patent Application No. 61/168,268, which was previously incorporated herein by reference in its entirety.

Molded Article Embodiment 1

In one embodiment of a molded article, according to the present invention, the molded article comprises a body and at least one or a plurality of 3-dimensional structural features (e.g., a cube, rib, ridge, solid or hollow needle, pin, fin, gear, channel, socket, bobbin, pump, chip carrier, switch, etc.), which are each integral with and extending or otherwise protruding out from the body. Each structural feature comprises at least one or a plurality of fine feature elements. Such fine feature elements can include, for example, a leading edge or tip of the 3-dimensional structural feature (e.g., the tip of a needle or pin, a gear tooth, opposite edges defining the opening of a channel, the bore of a hollow needle, the bore of a hollow microneedle in fluid communication with a microfluidic channel, etc.). Each fine feature element has a minor dimension, and the body or at least each structural feature consists of, consists essentially of, comprises, or is formed entirely, substantially (i.e., at least about 50% and preferably at least about 60%) or at least in part with, at least one melt processable or thermotropic liquid crystalline polymer (TLCP) having a plurality of molecularly sensitive mesogens. All or at least a substantial portion of the molecular mesogens across the minor dimension are in a flow aligned state (i.e., a state having a relatively anisotropic alignment compared to the alignment resulting from mesogen flow tumbling).

This molded article can be formed using any of the above methods. The body of this article can be formed using a body cavity in accordance with any of the above methods. The at least one structural feature of this article can also be formed using the at least one feature cavity in accordance with any of the above methods. In addition, the at least one fine feature element of this article can be formed using the at least one fine feature chamber in accordance with any of the above methods.

Molded Article Embodiment 2

A version of the molded article embodiment 1, wherein more than 50% of each structural feature is at least one TLCP.

Molded Article Embodiment 3

A version of the molded article embodiment 1 or 2, wherein at least about 30% of the TLCP mesogens across the minor dimension of each fine feature element are flow aligned. Depending on the article molded, each fine feature element is considered to have a substantial portion of its TLCP mesogens flow aligned, when at least about 30%, 35%, 40%, 45%, 50%, 55%, 60%, 65%, 70%, 75%, 80%, 85%, 90%, 95%, or 100% of the TLCP mesogens across the minor dimension of each fine feature element are flow aligned. Such a minor dimension can include, for example, the thickness of a wall, diameter of a needle tip, micro-needle tip, the bore or hole of a hollow needle or microneedle, the channels of a micro-fluidic channel, etc. For some applications (e.g., the tip of a micro-needle), it can be desirable to have a maximum of up to and including about 25% of the TLCP mesogens across the minor dimension of each fine feature element to be flow tumbled (i.e., for a maximum of about 25% of the minor dimension to be isotropic).

Molded Article Embodiment 4

A version of any one of the molded article embodiments 1 to 3, wherein the TLCP mesogens in each fine feature element exhibit an average flow alignment, as evidenced by an average anisotropy factor in the range of from at least about 0.3 up to and less than 1.0, and preferably an anisotropy factor in the range from about 0.4 to less than 1.0.

Molded Article Embodiment 5

A version of any one of the molded article embodiments 1 to 4, wherein the flow aligned TLCP mesogens across the minor dimension of each fine feature element exhibit an average molecular alignment, as evidenced by an average anisotropy factor in the range of from at least about 0.5 up to and less than 1.0, and preferably an anisotropy factor in the range from about 0.6 or 0.7 to less than 1.0.

Molded Article Embodiment 6

A version of any one of the molded article embodiments 1 to 5, wherein all or at least a substantial portion of the TLCP mesogens in the at least one structural feature are in a flow aligned state. That is, these TLCP mesogens have a relatively anisotropic alignment compared to the isotropic alignment caused by flow tumbling.

Molded Article Embodiment 7

A version of any one of the molded article embodiments 1 to 6, wherein at least about 10% of the TLCP mesogens in each structural feature are flow aligned, with the core or otherwise remainder of the TLCP mesogens in each structural feature having a relatively isotropic alignment, especially when compared to the flow aligned molecular mesogens in the at least one fine feature element. Depending on the article molded, each structural feature is considered to have a substantial portion of its TLCP mesogens flow aligned, when at least about 10%, 15%, 20%, 25%, 30%, 35%, 40%, 45%, 50%, 55%, 60%, 65%, 70%, 75%, 80%, 85%, 90%, 95%, or 100% of the TLCP molecular mesogens in each structural feature are flow aligned.

Molded Article Embodiment 8

A version of any one of the molded article embodiments 1 to 7, wherein the TLCP mesogens in each structural feature exhibit an average flow alignment, as evidenced by an average anisotropy factor in the range of from at least about 0.2 up to and less than 1.0, and preferably an anisotropy factor in the range from about 0.3 or 0.4 to less than 1.0.

Molded Article Embodiment 9

A version of any one of the molded article embodiments 1 to 8, wherein the flow aligned TLCP mesogens in each structural feature exhibit an average molecular alignment, as evidenced by an average anisotropy factor in the range of from at least about 0.5 up to and less than 1.0, and preferably an anisotropy factor in the range from about 0.6 or 0.7 to less than 1.0.

Molded Article Embodiment 10

A version of the molded article embodiment 7, wherein the remainder of the TLCP mesogens in each structural feature exhibit a random molecular alignment, as evidenced by an average anisotropy factor of less than 0.2, especially when compared to the flow aligned molecular mesogens in the at least one fine feature element.

Molded Article Embodiment 11

A version of the molded article embodiment 7, wherein the remainder of the TLCP mesogens in each structural feature are in a completely or at least substantially flow tumbled state. As used herein, the remainder of the TLCP molecular mesogens in each structural feature is considered to be in a substantially flow tumbled state when they exhibit an anisotropy factor of less than 0.2.

Molded Article Embodiment 12

Another version of the molded article embodiment 7, wherein about all of the remainder of the TLCP mesogens in each structural feature have a relatively isotropic alignment (e.g., have a flow tumbled state), especially when compared to the flow aligned molecular mesogens in the at least one fine feature element.

Molded Article Embodiment 13

A version of any one of the molded article embodiments 1 to 12, wherein about all, a substantial portion, or at least a portion of the TLCP mesogens in the body are in a flow aligned state. That is, these TLCP mesogens in the body have a relatively anisotropic alignment compared to the isotropic orientation state caused by flow tumbling.

Molded Article Embodiment 14

A version of any one of the molded article embodiments 1 to 13, wherein at least about 10% of the TLCP mesogens in the body are flow aligned, with the core or otherwise remainder of the TLCP mesogens in the body having a relatively isotropic orientation state, especially when compared to the flow aligned molecular mesogens in the at least one fine feature element. Depending on the article molded, the body is considered to have a substantial portion of its TLCP mesogens flow aligned, when at least about 10%, 15%, 20%, 25%, 30%, 35%, 40%, 45%, 50%, 55%, 60%, 65%, 70%, 75%, 80%, 85%, 90%, 95%, or 100% of the TLCP mesogens in the body are flow aligned. For many applications it could be difficult to obtain less than 10% flow aligned TLCP mesogens in the body.

Molded Article Embodiment 15

A version of any one of the molded article embodiments 1 to 14 wherein the TLCP mesogens in the body exhibit an average flow alignment, as evidenced by an average anisotropy factor in the range of from greater than zero up to and less than one, and preferably an anisotropy factor in the range from about 0.1 to less than 1.0.

Molded Article Embodiment 16

A version of any one of the molded article embodiments 1 to 15, wherein the flow aligned TLCP mesogens in the body exhibit an average molecular alignment, as evidenced by an average anisotropy factor in the range of from at least about 0.1 up to and less than 1.0.

Molded Article Embodiment 17

A version of the molded article embodiment 14, wherein the remainder of the TLCP mesogens in the body exhibit a random molecular alignment, as evidenced by an average anisotropy factor of less than 0.2, especially when compared to the flow aligned TLCP mesogens in the at least one fine feature element.

Molded Article Embodiment 18

Another version of the molded article embodiment 14, wherein the remainder of the TLCP mesogens in the body are in a flow tumbled state.

Molded Article Embodiment 19

A version of any one of the molded article embodiments 1 to 12, wherein about all of the TLCP mesogens in the body have a relatively isotropic orientation state (e.g., have a flow tumbled state), especially when compared to the flow aligned TLCP mesogens in the at least one fine feature element.

Molded Article Embodiment 20

A version of any one of the molded article embodiments 1 to 19, wherein the body does not form a portion of the molded article. For example, the body can be recycled or is otherwise disposable.

Molded Article Embodiment 21

The molded article of molded article embodiment 20, wherein the body forms a disposable sprue or runner.

Molded Article Embodiment 22

A version of any one of the molded article embodiments 1 to 21, wherein the minor dimension (e.g., a thickness) of the at least one fine feature element is less than or equal to about 500 micrometers ($\mu$m). It can be preferable, for some molded articles, for the minor dimension to be less than or equal to about 400 micrometers, 300 micrometers, 200 micrometers or even 100 micrometers. It can also be preferable for the minor dimension of at least one fine feature element to be at least 90 nanometers (nm) or to fall within the range of from about 90 nm up to and including about 20 microns.

Molded Article Embodiment 23

A version of the molded article embodiment 22, wherein the at least one fine feature element comprises a wall having a thickness of less than or equal to about 0.50 mm (500 microns).

Molded Article Embodiment 24

A version of the molded article embodiment 23, wherein the wall thickness of the at least one fine feature element is less than or equal to about 0.20 mm (200 microns).

Molded Article Embodiment 25

A version of any one of the molded article embodiments 1 to 24, wherein the at least one fine feature element is a plurality of fine feature elements, with each having an aspect ratio of greater than or equal to 10:1.

Molded Article Embodiment 26

A version of any one of the molded article embodiments 1 to 25, wherein the at least one fine feature element comprises an edge having an edge thickness of less than or equal to 800 nm.

Molded Article Embodiment 27

A version of any one of the molded article embodiments 1 to 24, wherein the at least one fine feature element is a plurality of fine feature elements, with each fine feature element comprising a tip radii less than or equal to 800 nm.

Molded Article Embodiment 28

A version of the molded article embodiments 1 to 21, wherein the minor dimension (e.g., thickness) of the at least one fine feature element is in the range of from about 90 nanometers (nm) up to and including about 20 microns.

Molded Article Embodiment 29

A version of any one of the molded article embodiments 1 to 28, wherein the at least one fine feature element defines a leading portion of a corresponding structural feature. For example, the fine feature element could be a leading edge or tip of the 3-dimensional structural feature (e.g., a needle or pin point, gear tooth, opposite edges defining the opening of a channel, the bore or hole of a hollow needle or micro-needle, etc.).

Molded Article Embodiment 30

A version of any one of the molded article embodiments 1 to 29, wherein each structural feature is defined entirely by at least one fine feature element.

Molded Article Embodiment 31

A version of any one of the molded article embodiments 1 to 30, wherein the thermotropic liquid crystalline polymer (TLCP) is completely or substantially unfilled with a filler or additive material (e.g. particles or fibers of glass, graphite, carbon, mineral, etc).

Molded Article Embodiment 32

A version of any one of the molded article embodiments 1 to 30, wherein the thermotropic liquid crystalline polymer (TLCP) is substantially or at least partially filled with a filler or additive material (e.g. particles or fibers of glass, graphite, carbon, mineral, etc).

Figure 2A:
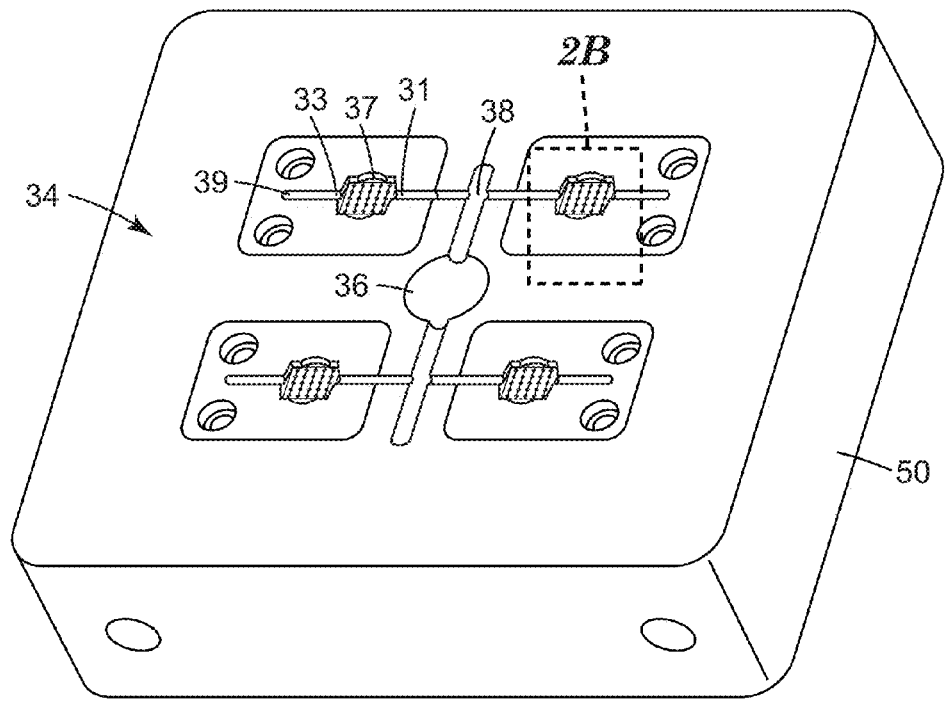
FIG. 2A is a perspective view showing the face of the mold cavity of a stacked laminate mold half of a cold runner injection molding device according to one embodiment of the present invention.
Figure 2B:
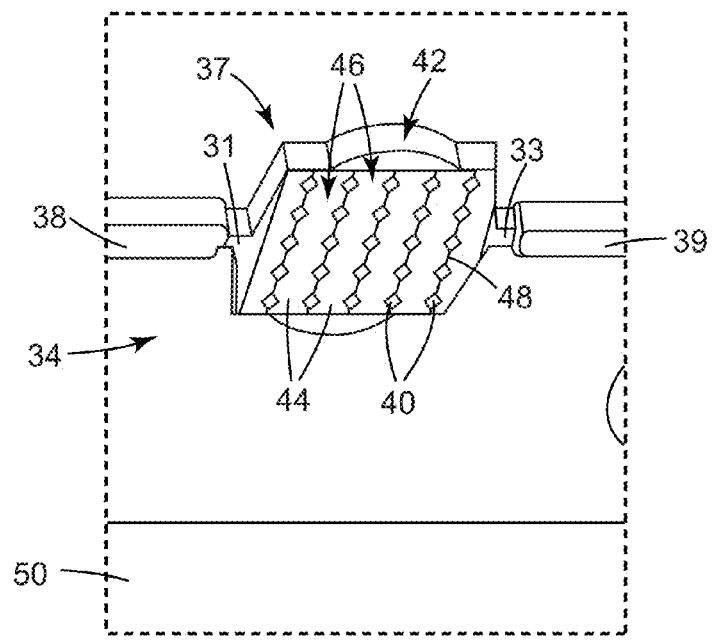
FIG. 2B is an enlarged view of the area 2B of the mold half of the cold runner injection molding device of FIG. 2A.
Figure 2C:
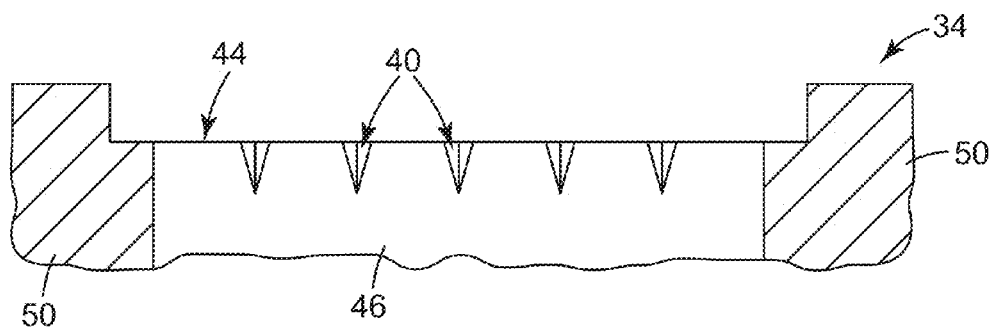
FIG. 2C is a cross sectional schematic end-view of the mold die half of FIG. 2A.

Referring to FIGS. 2A-2C, a cold runner die or mold comprises a first or stacked laminate mold half 34 and a second mold half (not shown) that together define a mold cavity that includes a sprue bushing passage 36 formed through the first mold half 34. The sprue bushing 36 receives a sprue (not shown) through which a molten composition is received. The molten composition from the sprue (not shown) is directed into four article cavities 37 through corresponding cold runner passages 38 via corresponding edge gate openings 31. The gates 31 determine the flow field of the molten composition injected into the corresponding article cavities 37. The mold cavity can include secondary edge gates 33 and runner passages 39 on the downstream side of each article cavity 37 to ensure macroscopic gas evacuation and balanced part ejection. Each of the illustrated article cavities 37 in FIG. 2B includes a plurality of feature cavities 40 (e.g., for forming solid or hollow microneedles) in fluid communication with a body cavity 42. The body cavity 42 includes a major face that is at least partially defined by exposed end surfaces 44 of a plurality of plates 46 stacked together tightly so as to make contact between opposing major surfaces 48 of adjacent plates 46. The plates 46 together form a stacked laminate or laminate mold held tightly together in intimate contact via physical or chemical means including, for example, clamping, bonding, or wedge blocking (e.g., see FIG. 5). The feature cavities 40 are defined by corresponding pyramidal-shaped notches (shown in phantom) formed in exposed surfaces 44 and major surfaces 48 of the plates 46. The plates 46 can be made of any suitable mold material such as, for example, steel (e.g., A2, M2, spring steel, H13, S7, 420 stainless steel, high carbon steel, etc.). Except for their exposed surfaces 44, the remainder of each plate 46 is hidden within the mold half 34, as indicated for some of the plates 46 by phantom lines. The mold half 34 can be formed in part by a block or frame 50 made of heat conductive metal (e.g., Beryllium Copper Moldstar® from Moldmax® Thermal Management Solutions, Southfield Mich.), which is used to maintain appropriate temperature control surrounding the mold cavity and provide good heat transfer for cooling of the molded article.

Figure 3A:
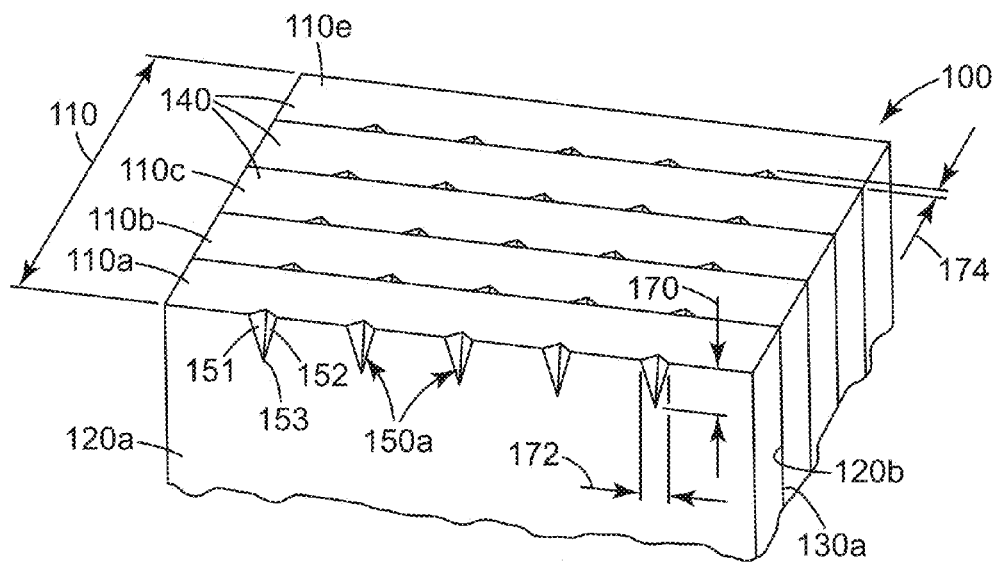
FIG. 3A is an isometric perspective view of one embodiment of a stacked laminate of mold half plates that can be used in the mold half of FIG. 2A.

Referring to FIG. 3A, another embodiment of a stacked laminate 100 of the present invention comprises plates 110a, 110b, 110c, . . . and 110e (collectively a plurality of plates 110) which are contacted together. Each plate comprises a first major surface and a second major surface. Typically, the first major surface and second major surface of each plate are planar, although this is not required so long as they are substantially conforming to one another. Plate 110a comprises first major surface 120a and second major surface 130a. Plurality of plates 110 are stacked adjacent to one another such that second major surface 130a of plate 110a is adjacent first major surface 120b of plate 110b. Plurality of plates 110 comprise first mold surface 140, wherein first mold surface 140 connects the first major surface and the second major surface of each plate. In one embodiment, the first major surface and the second major surface of each plate in the plurality of plates are parallel to one another as shown in FIG. 3A. In another embodiment, the first major surface and the second major surface of a plate in the plurality of plates are not parallel to one another and instead are tapered either in the horizontal direction, the vertical direction, or both directions. The adjacent plate is then tapered in the opposite direction so as to maintain substantial conformation between the second major surface of one plate and the first major surface of the adjacent plate. As depicted in FIG. 3A, it is desirable for first mold surface 140 of each of the plurality of plates 110 to be carefully formed so as to present a continuous, uninterrupted surface made up of each of the individual mold surfaces.

An exemplary formation of the cavities in the stacked laminate mold is as follows. The plurality of plates 110 comprise a plurality of cavities 150a. Each cavity 150a comprises a V-shaped groove comprising first planar cavity surface 151 and second planar cavity surface 152 meeting at apex 153. As shown in FIG. 3A, cavity 150a is open at least to first mold surface 140. First planar cavity surface 151 and second planar cavity surface 152 intersect each respective plate's first major surface (e.g., 120a) and each respective plate's first mold surface (e.g. 140). The resulting cavity shape is defined by the intimate contact between the first major surface and second major surface of adjacent plates. For example in FIG. 3B, stacked laminate 160 comprises a square pyramidal-shaped cavity defined by cavity 150b on first major surface 121 of plate 111e and cavity 155b on second major surface 131 of plate 111d. In FIG. 3C, a stacked laminate 170 of plates 172 comprises pyramidal-shaped microneedle feature cavities 174. Each feature cavity 174 has two long side walls 176 formed in one major surface of each plate 172 and two short side walls 178 formed in the opposite major surface of each plate 172.

Figure 3B:
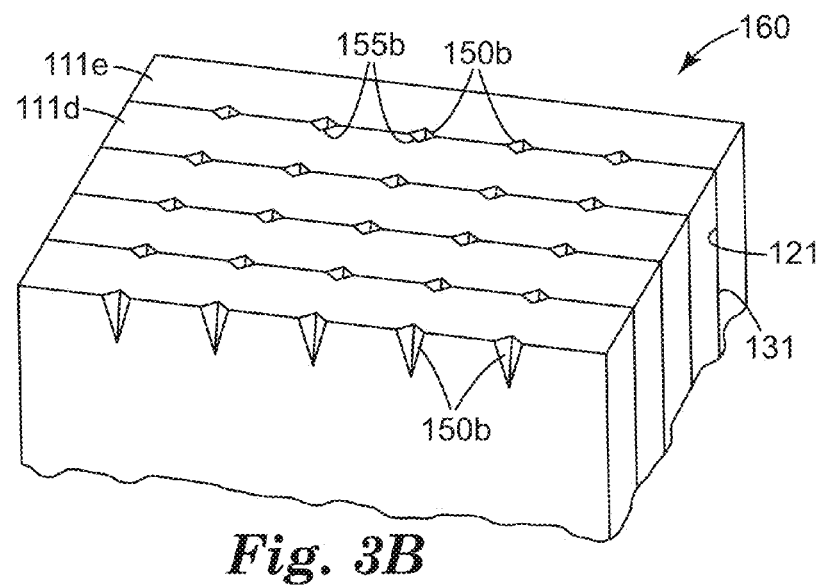
FIG. 3B is an isometric perspective view of another embodiment of a stacked laminate of mold half plates that can be used in the mold half of FIG. 2A.
Figure 3C:
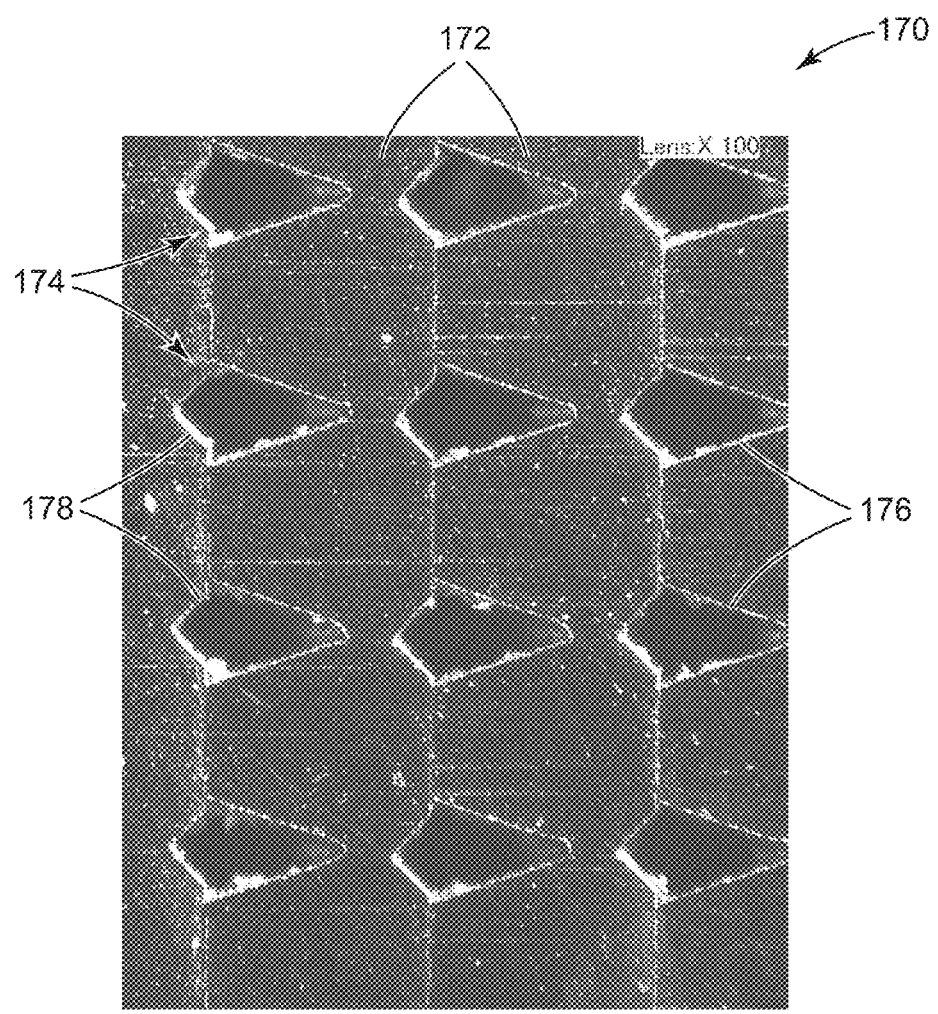
FIG. 3C is an enlarged top view of a photomicrograph of another embodiment of a stacked laminate of mold plates that can be used in the mold half of FIG. 2A.

The surface of the cavity can be planar as depicted in FIGS. 3A and 3B or curvilinear. The cavity may have any shape including, for example: a pyramid, a half pyramid, a stepped pyramid, a prism, a cone, a half cone, a stepped cone, a frustum, a standard bevel, short bevel or true short bevel hypodermic shape, a trilobal shape, obelisk, beveled cylinder, or combinations thereof. The shape and surface of the cavity is not particularly limited, however, the following may be considered when designing the cavity. First, the cavity shape may be limited by the ease of machining the cavity. Second, the cavity may be designed to facilitate the removal of the resulting molded article. For example, an appropriate draft angle greater than at least 0.5 degrees may be designed into the cavity shape to ensure proper removal of the resulting molded article from the mold. This is particularly important when the design involves a cavity having nearly straight walls. Third, the cavity may be designed to provide a resulting molded article that is effective for its intended function or purpose. For example, a solid or hollow microneedle array must be strong enough to pierce the subject's skin. The strength of the polymeric material used in the microneedle array may dictate the angle of the cavity, e.g., a greater angle would provide greater strength to the microneedle. However, this angular increase may cause greater trauma to the skin of the patient (or subject). Therefore, it may be important to provide a solid or hollow microneedle with a sharp tip and small surface area, which would require minimal force for the microneedle's tip to disrupt the surface of the stratum corneum. By molding such articles with a composition comprising a TLCP and substantially flow aligning the TLCP mesogens so as to produce relatively anisotropic physical properties (e.g, stiffness) in at least the microneedle's tip, microneedle cavities with lower angles can be used to form taller and narrower microneedles.

The dimensions of the microneedle cavity are defined with reference to FIG. 3A as follows. Cavity length 170 is defined as the distance along first major surface 120a from apex 153 to first mold surface 140. Cavity base width 172 is defined as the cavity distance along first mold surface 140 and the respective plate's major surface, e.g., 120a. Cavity base depth 174 is defined as the cavity distance along first mold surface 140, perpendicular to the respective plate's major surface. In some embodiments, such as FIG. 3B, the cavity base depth is the sum of the cavity base depth on adjacent plates.

When the mold cavity is enclosed, by mating the first mold half 34 with the corresponding second mold half (not shown), the article cavity 37 can be filled with molten composition such that the feature cavities 40 form solid pyramidal-shaped microneedles, and the body cavity 42 forms a support base from which the microneedles extend. This support base can be relatively rigid with a uniform thick wall structure (see, e.g., FIG. 6A), it can be relatively flexible with a uniform thin wall structure (see, e.g., FIG. 7A), or depending on the configuration of the mating surface of the second mold half that encloses the body cavity 42, the support base can be a wall structure having a variable thickness (see, e.g., FIG. 8A). Such a variable thickness wall structure can be made to be relatively flexible along one axis of the support base and relatively rigid along another axis at an angle (e.g., orthogonal) to the one axis of the support base.

The following Examples have been selected merely to further illustrate features, advantages, and other details of the invention. It is to be expressly understood, however, that while the Examples serve this purpose, the particulars of each Example are not to be construed in a manner that would unduly limit the scope of this invention.

EXAMPLES

Solid Microneedle with Uniform Rigid Wall Support Base

Mold Half A1

Figure 6A:
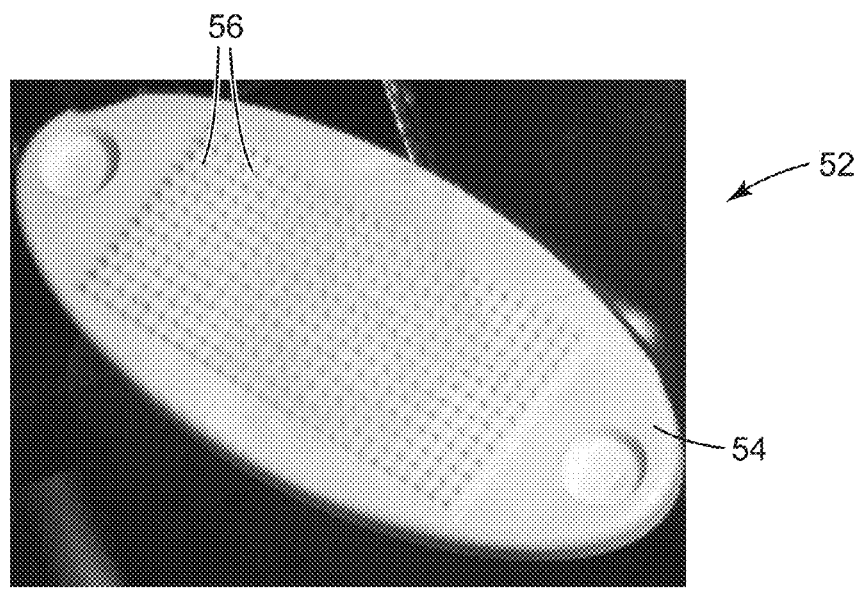
FIG. 6A is a top view of a molded article according to one embodiment of the present invention.
Figure 6B:
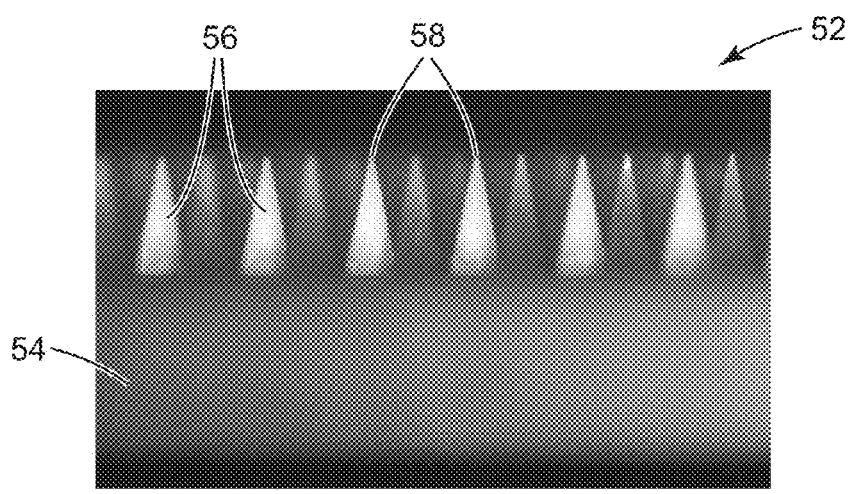
FIG. 6B is an enlarged side view of the molded article of FIG. 6A.

One embodiment of a hot runner mold for making solid microneedles extending out from a uniform rigid wall support base (e.g., as shown in FIGS. 6A and 6B) includes a first or stacked laminate mold half (Mold Half A1) made using fourteen steel plates 44 made of shock steel shim-stock, with the major surfaces 46 of each plate 44 having a surface roughness of approximately 0.25 RMS μm. Each plate was 13.80 mm in length, 10.70 mm in width, and 0.50 mm in thickness. Two holes were machined through the major surfaces of each plate to allow the plates to be pinned together using a wedge block laminate holder (like that shown in FIG. 5) and aligned to form a 13×27 array of spaced apart square pyramidal-shaped feature cavities (i.e., a total of 351 pyramidal-shaped cavities).

To form the molded article of FIGS. 6A and 6B, the stacked laminate mold half used included an oval-shaped body cavity having a 22.90 mm long major axis, a 11.00 mm long minor axis and a 0.76 mm thickness dimension. Individual feature cavities formed by a stacked laminate of plates, like those shown in FIG. 3B, were square pyramidal-shaped microneedle cavities, having four side walls, with a cavity length of 700 μm and a cavity side wall width of 200 μm. These feature cavity dimensions provide a cavity aspect ratio of 3.5:1. The microneedle feature cavities were spaced in a regular array with a distance of 508 μm between the apexes of the adjacent cavities. The apex of each microneedle feature cavity had a diameter of 10 μm or less. The microneedle formed in such feature cavity, according to the present invention, can have a tip with a radius of about 10 μm or less.

Mold Half B1

In making the molded article of FIGS. 6A and 6B, a hot runner manifold valve-gated system (Mold Half B1) from Incoe Corporation, Troy Mich., was used to meter the molten composition into the article cavities. The hot runner system includes valve gate nozzles, with actuating valve pins, for filling each article cavity with a desired amount of the molten composition. Each valve pin in the hot runner system measured 508 μm in diameter and was driven pneumatically using 150 psi compressed air to ensure rapid injection of the molten composition. Each valve pin was positioned at the center and perpendicular to the major face of the corresponding oval-shaped body cavity to symmetrically deliver molten composition to all portions of the body cavity and the connected microneedle feature cavities. A block of Beryllium Copper Moldstar® from Moldmax® Thermal Management Solutions, Southfield Mich., was used to maintain appropriate temperature control surrounding the hot runner valve gates. FIG. 2A shows a representative block shape, placement and dimensions.

Method 1 (Using Mold Halves A1 and B1)

In the method used to mold with the above described hot runner mold, the Mold Half A1 and Mold Half B1 were installed in a mold base of a 100-ton injection molding machine (Krauss-Maffei KM100-180CX, Krauss-Maffei Technologies GmbH, Munchen, Germany). As is common in the art, the parting line of the mold assembly had both primary and secondary vents for general air evacuation during injection of the molten composition. The sub-micrometer venting between the plates of the stacked laminate mold (e.g., as described for FIG. 5) provided additional venting, which enabled the high fidelity replication of the mold cavity fine features in the microstructure features of the molded article. Unfilled Vectra MT1300 TLCP pellets from Ticona Engineering Polymers, Florence, Ky., were loaded into a hopper and subsequently fed into a 15 mm reciprocating screw extruder to achieve the proper processing temperature of 540° F. (282° C.) in the melt state. Mold Half A1 and Mold Half B1 were heated to a temperature of 180° F. (82° C.), which is below the softening point of the TLCP. The molding cycle was initiated by closing Mold Half A1 with Mold Half B1. The molds were clamped together with 30 tons of force to form a clamped mold chamber. A first portion (approximately 90-95% of the article mold cavity or part size volume) of the total amount of molten composition from the reciprocating screw was injected into the clamped mold chamber. The first portion of molten composition was injected into the clamped mold chamber at a fixed velocity (hereafter referred to as the "injection velocity"). After injecting the first portion of the molten composition, the process was switched from an injection velocity driven to a pressure driven process by applying fixed pressure (hereafter referred to as the "pack pressure") to force the remainder of the molten composition into the mold cavity so as to fill the remainder of the article cavity. The pack pressure was applied for a fixed time (hereafter referred to as the "hold time"). The pack pressure was subsequently released and the mold chamber was cooled to an appropriate ejection temperature (hereafter referred to as the "mold temperature at ejection"), which was below the softening temperature of the TLCP. Details of the injection velocity, pack pressure, hold time, injection processing temperature, and ejection temperature used for each example are given in Table 1.

Molded Article Examples 1 to 10

Method 1 was used with the injection velocity, pack pressure, hold time, injection processing temperature, and mold temperature at ejection as listed in Table 1. The resulting average bulk anisotropy factor, microneedle anisotropy factor, average microneedle height, percent of filled needles, and average tip radii for each example is also shown in Table 1. The "average bulk anisotropy" factor is the average degree of orientation between the skin and core layers across a thickness of the molded article. The microneedle anisotropy factor is the average degree of orientation across the mid-section of a molded microneedle. The percent of filled needles defines the total number of microneedles made as a percentage of the total number of available microneedle cavities. The dimensions of the solid microneedles molded were measured via stereomicroscopy and scanning electron microscopy (SEM). Cryogenically frozen microtomed samples were analyzed using SEM to characterize the average bulk anisotropy factor and the microneedle anisotropy factors. The microneedle height and tip radii were compared between the fine feature cavity shape and the resulting molded article from Examples 1-10. The results of this comparison showed average part-to-part reproducibility of 97%. This value suggests that 3% of the cavity was not fully replicated in the TLCP over the range of conditions tested. Measurements were taken as an average of nine measurements (three from each individual array) and evaluated the solid microneedle base diameter compared to the cavity base diameter, the microneedle height compared to the cavity length, and the microneedle tip radii compared to the fine feature cavity tip radii.

TABLE 1

| Ex. No. | Injection Velocity [inches/sec, (mm/sec)] | Pack Pressure [psi, (MPa)] | Hold Time [sec] | Injection Processing Temp [° F., (° C.)] | Mold Temp at Ejection [° F., (° C.)] | Average Bulk Anisotropy Factor | Average Needle Anisotropy Factor | Average Needle Height [μm] | Percent Needles Filled [%] | Average Needle Tip Radii [μm] |
|---|---|---|---|---|---|---|---|---|---|---|
| 1 | 3.25 (82.6) | 10000 (68.9) | 1 | 540 (282) | 180.0 (82.2) | 0.30 | 0.75 | 685 | 94 | 8.3 |
| 2 | 3.25 (82.6) | 10000 (68.9) | 4 | 540 (282) | 180.0 (82.2) | 0.35 | 0.82 | 692 | 96 | 6.5 |
| 3 | 4.00 (101.6) | 10000 (68.9) | 4 | 540 (282) | 180.0 (82.2) | 0.45 | 0.85 | 695 | 98 | 2.2 |
| 4 | 4.00 (101.6) | 15000 (103.4) | 4 | 555 (282) | 180.0 (82.2) | 0.50 | 0.89 | 702 | 100 | 0.8 |
| 5 | 4.00 (101.6) | 15000 (103.4) | 2 | 555 (291) | 180.0 (82.2) | 0.46 | 0.86 | 698 | 99 | 1.5 |
| 6 | 4.00 (101.6) | 15000 (103.4) | 2 | 540 (282) | 160.0 (71.1) | 0.38 | 0.72 | 674 | 92 | 7.4 |
| 7 | 8.00 (203.2) | 15000 (103.4) | 2 | 540 (282) | 160.0 (71.1) | 0.55 | 0.88 | 696 | 96 | 5.3 |
| 8 | 4.00 (101.6) | 15000 (103.4) | 2 | 540 (282) | 200.0 (93.3) | 0.48 | 0.85 | 690 | 98 | 3.4 |
| 9 | 3.25 (82.6) | 15000 (103.4) | 2 | 555 (291) | 200.0 (93.3) | 0.38 | 0.74 | 687 | 98 | 5.2 |
| 10 | 3.25 (82.6) | 10000 (68.9) | 2 | 555 (291) | 200.0 (93.3) | 0.38 | 0.74 | 687 | 98 | 5.2 |

Examples 1-10 illustrate using a TLCP composition and stacked laminate tooling to injection mold solid microneedle arrays. The ability to rapidly promote shear induced orientation (i.e., flow alignment) of the TLCP mesogens during flow into the body cavity and/or the microneedle feature cavities allows for a high degree of orientation across the bulk thickness of the molded article body and even higher anisotropy within each of the microneedle features. While higher pack pressures and hold times led to higher average values of the bulk anisotropy factor, the greatest impact on orientation (i.e., alignment) of the mesogens was due to increased injection flow velocity. Higher flow velocities within the microneedle feature cavities can retard the onset of flow tumbling of the mesogens in the TLCP and thus promoted a flow aligned state. This flow aligned state of the mesogens subsequently translated into stronger unidirectional mechanical properties of the microneedles in the final molded article.

The combined data for Examples 1-10 indicates that the solid microneedles in the molded arrays had an average height of 691 μm (+/−5 μm) and an average tip radius of 4.6 μm (+/−1 μm).

Comparison between the shape of the feature cavity and the resulting molded article from Examples 1-10 shows an average part-to-part reproducibility of about 97%. This value suggests that 3% of the cavity was not fully replicated in the TLCP composition over the range of conditions tested. An average of nine measurements were taken (i.e., three molded microneedles from each of 3 individual arrays) and evaluated to compare the solid microneedle base diameter to the cavity base diameter; to compare the microneedle height to the cavity length, and to compare the microneedle tip radii to the fine feature cavity tip radii.

Referring to FIGS. 6A and 6B, a solid microneedle article or array 52 of Example 4 was molded according to Method 1 and viewed under an optical microscope (Olympus SZX12, Olympus America Inc., Center Valley, Pa.). The solid microneedle array 52 comprises an oval-shaped support base or body 54 and a plurality of solid microneedles 56. The body 54 is relatively thick and rigid measuring 762 μm in cross-sectional thickness (e.g., compared to the body 62 in FIGS. 7A-7C with a cross-sectional thickness of 100 μm). Each microneedle 56 has a fine tip feature 58. As shown in FIG. 6B, the tips 58 of two solid microneedles 56 have a radius of approximately 5 μm. Dimensions for the microneedle tips 58 as low as about 800 nm have been observed.

Solid Microneedle with Uniform Thin Wall Support Base
Mold Half A2

Figure 7A:
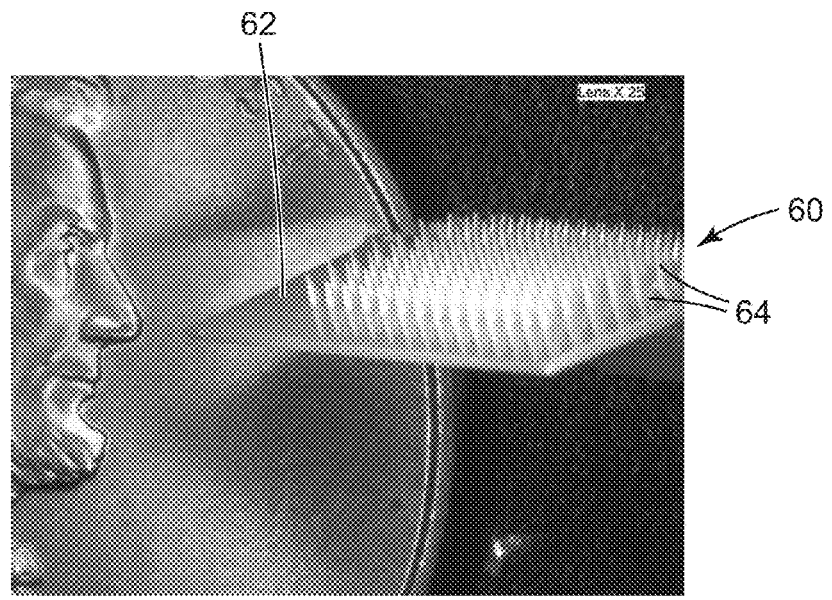
FIG. 7A is a perspective view of a molded article according to another embodiment of the present invention, with a flexible body.
Figure 7B:
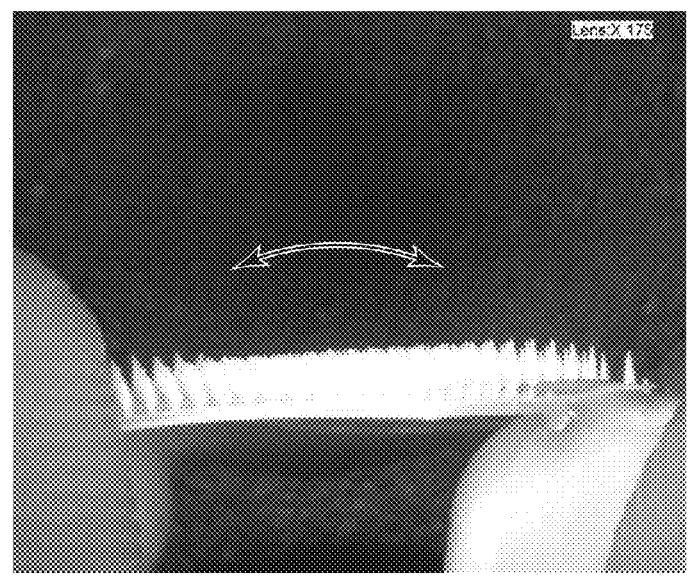
FIG. 7B is a side view of the molded article of FIG. 7A with its body flexed along one direction.
Figure 7C:
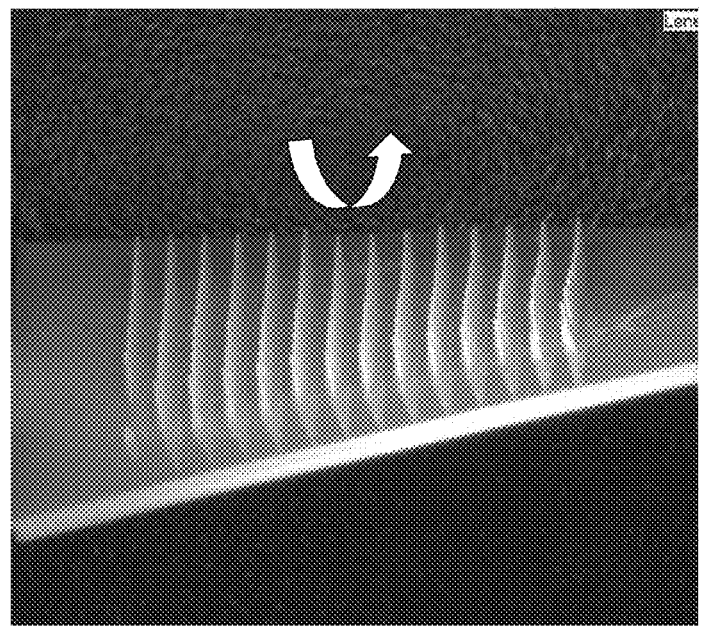
FIG. 7C is a side view of the molded article of FIG. 7A with its body flexed along a direction orthogonal to the direction the body is flexed in FIG. 7B.

An embodiment of a mold for making solid microneedles extending out from a uniform thin wall support base (e.g., as shown in FIGS. 7A-7C) includes a first or stacked laminate mold half ("Mold Half A2") made using twenty steel plates made of A2 steel shim-stock, with the major surfaces of each plate having a surface roughness of approximately 0.30 RMS μm. Each plate was 10.00 mm in length, 10.00 mm in width, and 0.50 mm in thickness. Two holes were machined through the major surfaces of each plate to allow the plates to be pinned together using a wedge block laminate holder (like that shown in FIG. 5) and aligned to form a 14×14 array of spaced apart pyramidal-shaped feature cavities (i.e., a total of 196 square pyramidal-shaped cavities).

To form the molded article of FIGS. 7A-7C, the stacked laminate mold half used included a square-shaped body cavity having a length of 10.00 mm for each side wall. A movable wall insert on the face of the body cavity defined several thickness dimensions for the support base ranging from 0.25 mm (thickest) and 0.10 mm (thinnest). Individual feature cavities on the stacked laminate mold half were that of a pyramidal-shaped microneedle having two long side walls each measuring 350 μm and two short side walls each measuring 140 μm (see FIG. 3C), all four side walls converging to a final cavity length of 500 μm. The microneedle feature cavities were spaced in a regular array with a distance of 508 μm between the apexes of the adjacent cavities. The apex of the microneedle feature cavity had a diameter of 5 μm or less. The microneedle formed in such feature cavity, according to the present invention, can have a tip with a radius of about 5 μm or less.

Mold Half B2

In making the molded article of FIGS. 7A-7C, a cold runner plate ("Mold Half B2") was used to channel the molten composition into the mold cavities. The cold runner plate included a sprue passage for directing molten composition into a plurality of the article cavities through corresponding cold runner passages via corresponding edge gate openings. A block of Beryllium Copper Moldstar® from Moldmax® Thermal Management Solutions, Southfield Mich., was used to maintain appropriate temperature control surrounding the cold runner plate and provide good heat transfer for cooling of the molded article. A representative block shape, placement and dimensions is shown in FIG. 2A.

Method 2 (Using Mold Halves A2 and B2)

Method 1 was used to mold with Mold Half A2 and Mold Half B2. The following molding parameters were used: injection velocity of 304.8 mm/sec, pack pressure of 137.8 MPa, hold time of 3 sec, injection processing temperature of 540° F. (282° C.), and mold temperature at ejection of 85° C.

Referring to FIGS. 7A-7C, a solid microneedle article or array 60 of Example 11 was molded according to Method 2 and comprises a uniform thin wall support base or body 62 and a 14×14 array of solid microneedles 64. The body 62 has a thickness of about 100 μm. Because body 62 is so thin, a large percentage of the mesogens flowing through the body cavity forming body 62 will end up in a flow aligned state inside of body 62. The curving arrows in FIGS. 7B and 7C show how the relatively thin body 62 can be bent or flexed even though the body 62 has a high concentration of flow aligned mesogens therein. This example illustrates that even though flow aligned mesogens can stiffen or otherwise cause the TLCP to behave in an anisotropic manner, the anisotropic element(s) of the molded article (e.g., the body 62) can be designed so as to eliminate or at least reduce anisotropic characteristics that may be undesirable for that particular element. In this way, the body 62 can still be flexible. The solid microneedles 64 had an average height of about 495 μm and an average tip radius of about 3 μm.

Solid Microneedle with Variable Wall Thickness Support Base
Mold Half A3

Figure 8A:
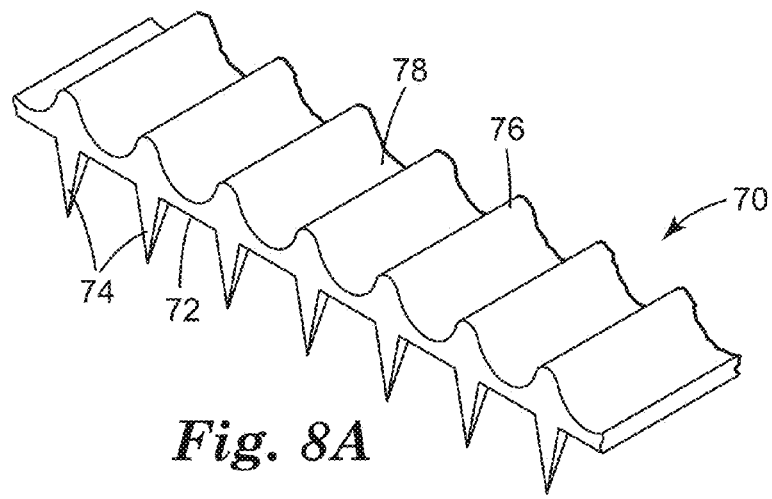
FIG. 8A is a partial perspective view of the back of a molded article according to another embodiment of the present invention.
Figure 8B:
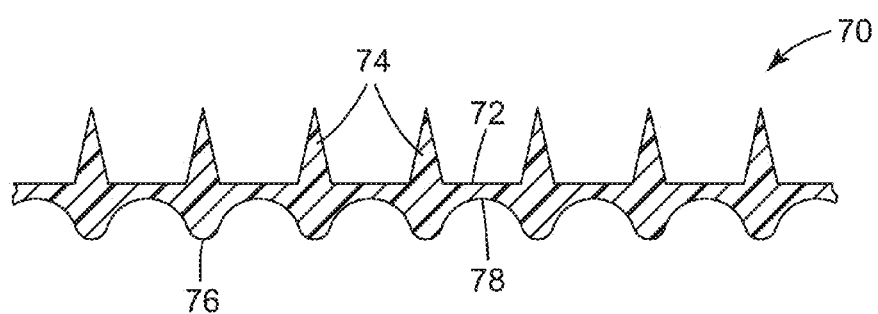
FIG. 8B is a cross sectional side view of the molded article of FIG. 8A.
Figure 8C:
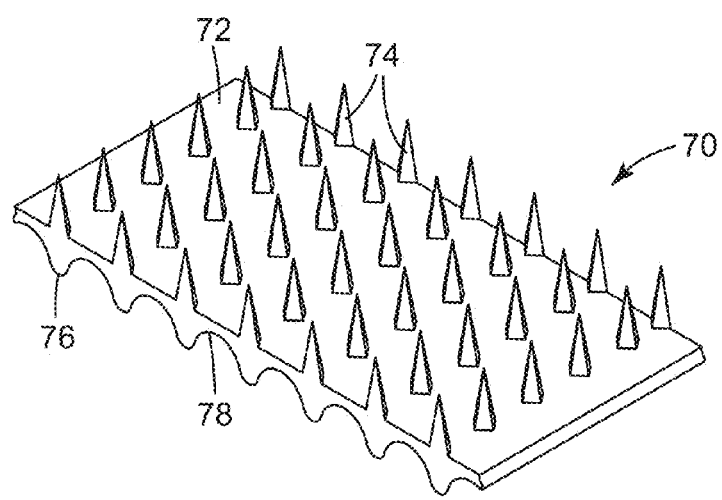
FIG. 8C is a perspective view of the top of the molded article of FIG. 8A.

An embodiment of a mold for making solid microneedles extending out from a support base having a variable wall thickness (e.g., as shown in FIGS. 8A-8C) includes a first or stacked laminate mold half ("Mold Half A3") made using a stacked laminate comprising thirty two steel plates made of P20 stainless steel, with the major surfaces of each plate having a surface roughness of approximately 0.20 RMS μm. The dimensions of each plate were: 25.40 mm in length, 15.00 mm in width, and 1.00 mm in thickness. Two holes were machined through the major surfaces of each plate to allow the plates to be pinned together using a wedge block laminate holder (like that shown in FIG. 5) and aligned to form a 13×25 array of spaced apart prism-shaped feature cavities (i.e., a total of 325 prism-shaped cavities).

To form the molded article of FIGS. 8A-8C, the stacked laminate mold half used included a rectangular-shaped body cavity with a long wall dimension of 25.40 mm and a short wall dimension of 12.70 mm. A movable wall insert on the face of the body cavity defined a series of valleys with variable thickness dimensions ranging from 0.50 mm (thickest) to 0.05 mm (thinnest). Individual microneedle feature cavities on the stacked laminate mold half were that of a prism-shaped microneedle having three sidewalls each measuring 350 μm, all three side walls converging to a final cavity length of 900 μm (see FIG. 3A). The microneedle feature cavities were spaced in a regular array with a distance of 254 μm between the apexes of the adjacent cavities. The apex of each microneedle feature cavity had a diameter of 1 μm or less. The microneedle formed in such feature cavity, according to the present invention, can have a tip with a diameter of about 1 μm or less.

Mold Half B3

In making the molded article of FIGS. 8A-8C, a cold runner plate ("Mold Half B3") was used to channel the molten composition into the mold cavities. The cold runner plate included a hot tip sprue bushing for directing molten composition directly to a fan gate that fed the molten composition into a plurality of the article cavities through the short dimension of the corresponding rectangular body cavity. A block of Beryllium Copper Moldstar® from Moldmax® Thermal Management Solutions, Southfield Mich., was used to maintain appropriate temperature control surrounding the cold runner plate and provide good heat transfer for cooling of the molded article. FIG. 2A shows a representative block shape, placement and dimensions.

Method 3 (Using Mold Halves A3 and B3)

Method 1 was used to mold with Mold Half A3 and Mold Half B3. The following molding parameters were used: injection velocity of 177.8 mm/sec, pack pressure of 103.4 MPa, hold time of 2 sec, injection processing temperature of 550° F. (288° C.), and mold temperature at ejection of 80° C.

Referring to FIGS. 8A-8C, a solid microneedle article or array 70 of Example 12 was molded using Method 2. The array 70 comprises a variable thickness wall support base or body 72 and a 13×25 array of solid microneedles 74. The body 72 has alternating thicker regions or ridges 76 and thinner regions or grooves 78 along its length. The ridges 76 and grooves 78 run transversely across the entire width of the article 70. The body 72 has a thickness of about 175 µm at the thickest regions 76 and a thickness of about 54 µm at the thinnest regions 78. The solid microneedles 74 had an average height of about 890 µm and average tip radius of about 1 µm.

Gear with Micro-Size Gear Features

Mold Half A4

The present invention may also be used to make a wide variety of different size articles including, for example, a gear (e.g., spur gears, helical gears, worm gears, bevel weel, worm wheel, spiral bevel gears, internal gears, antibacklash gears, etc.) with micrometer or smaller size gear teeth extending out from a hub. Such a gear may also be made with other micrometer or smaller gear features, besides gear teeth (e.g., a gear drive shaft, gear spokes and walls, etc.). An embodiment of a mold (not shown) for making such a micro-featured gear may include a nickel electroform mold insert, or any other conventional mold insert, ("Mold Half A4") defining the desired gear-shaped body cavity with a plurality of gear teeth and other gear features. A nickel electroform mold insert may be desired because it can replicate features from a master to create fine feature cavity shapes in the final mold. The surface of the gear-shaped cavity of the nickel mold should be smooth with a surface roughness, e.g., of approximately 0.10 RMS µm. The gear produced using this mold can have a diameter of 1.00 mm and a thickness of 1.00 mm, with twelve gear teeth. Each gear tooth can have a measured thickness of about 5 µm or smaller at the narrowest point along the leading tip.

In making the molded gear, a cold runner plate ("Mold Half B4") was used to channel the molten composition into the mold cavities. The cold runner plate included a sprue passage for directing molten composition into a plurality of the article cavities through corresponding cold runner passages via corresponding tunnel gate openings. A block of Beryllium Copper Moldstar® from Moldmax® Thermal Management Solutions, Southfield Mich., was used to maintain appropriate temperature control surrounding the cold runner and provide good heat transfer for cooling of the molded gear. FIG. 2A shows a representative block shape, placement and dimensions.

Method 4 (Using Mold Halves A4 and B4)

Method 1 was used to mold with Mold Half A4 and Mold Half B4. The following molding parameters were used: injection velocity of 101.6 mm/sec, pack pressure of 55.2 MPa, hold time of 1 sec, injection processing temperature of 565° F. (296° C.), and mold temperature at ejection of 90° C.

Exemplary Compositions

The Thermotropic liquid crystal polymer (TLCP) material used in the above Examples 1-10 was commercially available unfilled Vectra® A950 natural. Vectra A (from Ticona-Celanese) is a random copolyester consisting of 27% hydroxynaphthoic acid (HNA) and 73% hydroxybenzoic acid (HBA). Unfilled resin was chosen in order to maximize the degree of orientation degradation due to director tumbling and to prevent masking of the inherent hydrodynamic effects due to the presence of fillers. The as received material in extruded pellet form was vacuum dried for 4-6 hours at 150° C. to ensure desirable moisture removal prior to molding. Experiments with Vectra MT1300 were also conducted. Vectra MT1300 is the Class VI medical grade version of Vectra A with the same chemistry.

TLCP pellets available from Vectra MT1300, Ticona Engineering Polymers, Florence Ky. were used for Examples 11 and 12. The TLCP pellets had the following material characteristics (taken from the literature):

1) a tensile modulus of 10600 MPa (megaPascal) when measured according to ISO 527-2;
2) a tensile stress at break of 182 MPa when measured according to ISO 527-2;
3) a tensile strain at break of 3.4% when measured according to ISO 527-2;
4) a flexural modulus of 9100 MPa when measured according to ISO 178;
5) a deflection temperature of 187° C. under a load of 1.8 MPa when measured according to ISO 75-2;
6) a vicat softening temperature of 145° C. melting when measured according to ISO 306 at a rate of 50° C./hr; and
7) a melting temperature of 280° C. when measured according to ISO 11357-3 at a rate of 10° C./min.

30% glass filled TLCP pellets available from Vectra MT1310, Ticona Engineering Polymers, Florence Ky. were also used for Examples 1-12. The TLCP pellets had the following material characteristics (taken from the literature):

1) a tensile modulus of 15000 MPa when measured according to ISO 527-2;
2) a tensile stress at break of 190 MPa when measured according to ISO 527-2;
3) a tensile strain at break of 2.1% when measured according to ISO 527-2;
4) a flexural modulus of 15000 MPa when measured according to ISO 178;
5) a deflection temperature of 235° C. under a load of 1.8 MPa when measured according to ISO 75-2;
6) a vicat softening temperature of 160° C. melting when measured according to ISO 306 at a rate of 50° C./hr; and
7) a melting temperature of 280° C. when measured according to ISO 11357-3 at a rate of 10° C./min.

40% mineral filled TLCP pellets available from Vectra MT4350, Ticona Engineering Polymers, Florence Ky. were also used for Examples 1-12. The TLCP pellets had the following material characteristics (taken from the literature):

1) a tensile modulus of 9800 MPa when measured according to ISO 527-2;
2) a tensile stress at break of 105 MPa when measured according to ISO 527-2;
3) a tensile strain at break of 3.2% when measured according to ISO 527-2;

4) a flexural modulus of 10000 MPa when measured according to ISO 178;

5) a deflection temperature of 230° C. under a load of 1.8 MPa when measured according to ISO 75-2; and 6) a melting temperature of 335° C. when measured according to ISO 11357-3 at a rate of 10° C./min.

30% mineral reinforced TLCP pellets available from Zenite SC260 NC010, DuPont Engineering Polymers, Wilmington Del. were also used for Examples 1-12. The TLCP pellets had the following material characteristics (taken from the literature):

1) a tensile modulus of 10000 MPa when measured according to ISO 527;

2) a tensile stress at break of 130 MPa when measured according to ISO 527;

3) a tensile strain at break of 5% when measured according to ISO 527-2;

4) a flexural modulus of 7100 MPa when measured according to ISO 178;

5) a deflection temperature of 245° C. under a load of 1.8 MPa when measured according to ISO 75-2; and 6) a melting temperature of 335° C. when measured according to ISO 11357-3 at a rate of 10° C./min.

Mold Design Guidelines

Balanced or isotropic properties (i.e., non-aligned or flow tumbled mesogens) in a body (e.g., a thick wall section of 750 μm or greater) of an article, molded according to the present invention, can be obtained while features (for example, microneedles) on the surface of the article body exhibit anisotropic properties (i.e., flow aligned mesogens), by significantly reducing the minor dimension or otherwise restricting the cross section of the mold cavity as the molten TLCP transitions from the body cavity to the feature cavities or at least to the fine feature chambers. For example, the confined, tapering wall geometry of a microneedle tip or fine feature cavity, as shown in FIG. 4B, can cause such a change in properties (i.e., mesogen alignment). Local velocity profiles that result from how the mold fills with the molten TLCP composition can lead to a complex kinematic behavior that incorporates two modes of orientation, namely shear and extensional character. When the minor dimension of a mold cavity is narrow enough, or the cavity cross section otherwise sufficiently restricted, the resulting shear force exerted on the molten composition is inhomogeneous and can be characterized by superimposed extension arising from changes in the cavity cross-section. The competition between shear and extension during the filling of the mold cavity can dramatically affect the molecular orientation (i.e., alignment) of the TLCP mesogens. This molecular orientation of the TLCP mesogens can also be intimately impacted by the concurrent solidification process occurring in the mold cavity. Through pressure-driven flow control via injection velocity, it is possible to tailor the final orientation (i.e., alignment) state of the TLCP mesogens in the molded article and produce a part with the desired balance of physical properties. This new understanding has enabled the production of parts with relatively thick (e.g., 0.75 mm to 1.0 mm) molded land or body elements that render a relatively equal distribution of 'shear' and 'transverse' properties (e.g., tensile properties), while also molding structural features (e.g., microneedle arrays on the surface of the body) or at least fine feature elements (e.g., microneedle tips) with 'in-shear' TLCP mesogen orientation states characterized by anisotropic properties along the flow direction of the molten composition filling the structural feature or fine feature element (e.g., enhanced tensile properties along the longitudinal axis of the needle and/or the needle tip).

Orientational Dynamics

TLCP director orientation (i.e., the orientation of the TLCP mesogens) can be controlled by controlling the velocity at which the molten composition is injected during the filling of the body cavity of the mold (i.e., during the $1^{st}$ stage of the injection molding cycle). While geometric constraints in the article cavity and other mold cavities (e.g., runners) can lead to shear induced orientation, the natural tendency for the mesogens in the molten TLCP to tumble under flow, ultimately deteriorates the feral mechanical anisotropy in the molded part. The following are a number of ways TLCP mesogen orientation can be controlled, such that flow tumbling can be mitigated and flow alignment can be promoted.

Prior to melt injection into the mold, the molten composition should not be left in the injector barrel for too long a period of time (e.g., typically no longer than about 1 minute). Otherwise, transesterification reactions coupled with the formation of stable, higher order melting crystallites could occur, which would hinder development of mesogen orientation under flow.

Injecting the molten composition at very fast velocities (e.g., on the order of about 3 to about 12 inches/second) can rapidly promote a flow aligned orientation state of the TLCP mesogens and mitigate the onset of flow tumbling. Profiling of the velocity in stages is possible if larger shot sizes are available. An electrical, servo driven injection system is preferred in order to enable the fastest screw acceleration for any given shot size.

The mold (e.g., the mold base and any mold inserts) should be kept at an equilibrium temperature (e.g., above about 45° C. but below about 150° C.) that allows enough shear thinning of the molten composition, moving through the mold cavity, to ensure the molten composition has a sufficiently low viscosity to adequately fill the mold cavity.

Figure 9:
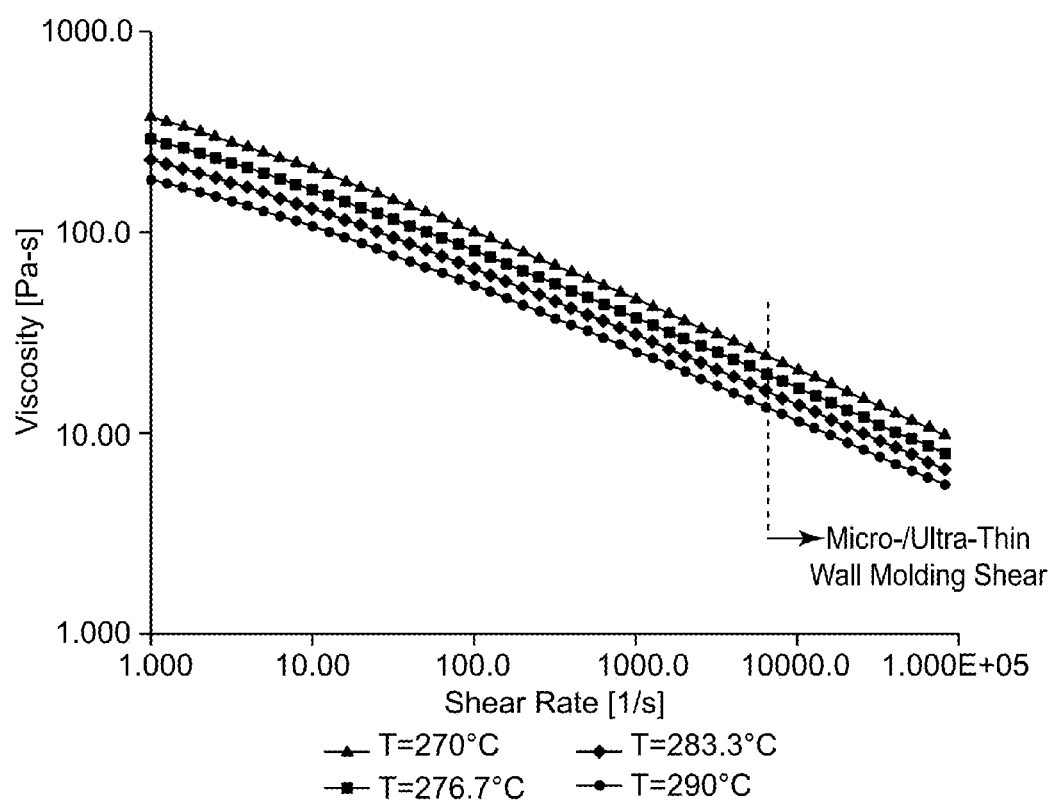
FIG. 9 is a graph illustrating the range of shear-viscosities for the TLCP Vectra A at various processing temperatures.

Typical viscosities on the order of 70 Pa s down to 20 Pa·s are possible when very high shear rates are exhibited at the gate of the mold. Tab, edge and tunnel gates can all be allowable configurations. FIG. 9 illustrates the range of shear-viscosities for the TLCP Vectra A at various processing temperatures. For the molding of articles with micro-sized features, such as the ones described here, the shear rate range can be above 10K 1/s.

To lock in the flow aligned orientation state of the TLCP mesogens, crystallization of the TLCP in the mold cavity should happen over a tune frame that is shorter than the critical relaxation time of the nematic polymer network (i.e., of the flow aligned mesogens). For the TLCP Vectra A, this time was determined to be no less than (i.e., greater than or equal to) 1.5 sec after injection of molten composition fills the article cavity. By applying positive hold and pack pressure shortly after the injection (approximately 0.2 sec fill time) this ensures that the rapidly solidifying melt entering the mold quickly adopts the shape of the cavity while locking the 'in-shear' orientation field given the rapid crystallization rate. Rate of crystallization can be controlled by tuning the mold temperature and injection pressure to achieve the proper development of flow that helps impede polymer chain (i.e., mesogen) relaxation.

When a $2^{nd}$ stage of the molding cycle (pack pressure stage) is used, it can be possible to fill the remainder of each micro-cavity down to the sharpest point cavity available in the mold.

For the case of the microneedles presented here, TLCP molding replication down to 800 nm at the sharpest point has been observed as a result of several factors that include:

(1) Development of flow aligned molecular nematic (i.e., mesogen) orientation state during $1^{st}$ stage mold fill.
(2) Use of very fast velocities during the filling of the article cavity, which can induce a high degree of anisotropy in the TLCP mesogens, and which in turn can help reduce the local melt viscosity in the cavity.
(3) Locking in the TLCP mesogen orientation due to fast crystallization dynamics in the mold.
(4) Proper venting of any entrapped air via micro-cavity venting.
(5) Availability of mold tooling with sub-micron feature cavity resolution and tolerances.

This invention may take on various modifications and alterations without departing from its spirit and scope. Accordingly, this invention is not limited to the above-description but is to be controlled by the limitations set forth in the following or future claims and any equivalents thereof.

What is claimed is:

1. A method of molding an article, said method comprising:
    providing a composition comprising at least one thermotropic liquid crystalline polymer (TLCP), with the TLCP comprising a plurality of mesogens;
    providing a mold comprising a mold cavity, with the mold cavity comprising at least one feature cavity, and each feature cavity comprising at least one fine feature chamber having a minor dimension up to 100 micrometers;
    heating the composition so as to form molten composition comprising molten TLCP;
    filling the mold cavity and the at least one feature cavity with a desired amount of the molten composition such that the molten composition filling a body cavity is moving at a first flow velocity that causes at least some flow tumbling of mesogens in the corresponding molten TLCP, and the molten composition filling the at least one fine feature chamber is moving at a second flow velocity that is faster than the first flow velocity and that causes flow alignment of at least a portion of the mesogens in the corresponding molten TLCP relative to a flow direction of the moving molten composition; and
    solidifying the molten composition such that mesogens of at least the solidified TLCP in the at least one fine feature chamber substantially maintain their flow alignment.

2. The method of claim 1, wherein the first flow velocity of the molten composition filling the body cavity is less than or equal to 108 mm/s.

3. The method of claim 1, wherein the flow velocity of the molten composition filling the at least one fine feature chamber is at least 51 mm/s.

4. The method of claim 1, wherein the at least one fine feature chamber has a minor feature dimension in the range of from 100 nm up to and including 20 microns.

5. The method of claim 1, wherein the difference between the first flow velocity and the second flow velocity is at least 12.7 mm/s.

6. The method of claim 1, wherein the mesogens of the TLCP solidified in the at least one fine feature chamber are molecularly aligned, relative to the flow direction of the moving molten composition filling the at least one fine feature chamber, by an anisotropy factor in the range of from greater than 0.4 up to 1.0.

7. The method of claim 1, wherein the molded article comprises a body and at least one 3-dimensional structural feature integral with and protruding out from said body, said at least one structural feature comprising at least one fine feature element having a minor dimension up to 100 micrometers, and said at least one structural feature comprising at least one thermotropic liquid crystalline polymer (TLCP) having a plurality of mesogens, with at least a portion of the mesogens across said minor dimension being in a flow aligned state.

8. The method of claim 7, wherein for the article, at least 30% of the TLCP mesogens across the minor dimension of each fine feature element are flow aligned.

9. The method of claim 7, wherein for the article, the TLCP mesogens in each fine feature element exhibit an average anisotropy factor in the range of from at least 0.3 up to and less than 1.0.

10. The method of claim 7, wherein for the article, the flow aligned TLCP mesogens across the minor dimension of each fine feature element exhibit an average anisotropy factor in the range of from at least 0.5 up to and less than 1.0.

11. The method of 7, wherein for the article, at least 10% of the TLCP mesogens in each structural feature are flow aligned, with the remainder of the TLCP mesogens in each structural feature having a relatively isotropic orientation state.

12. The method of claim 7, wherein for the article, the minor dimension of said at least one fine feature element is less than or equal to 500 µm.

13. The method of claim 7, wherein for the article, the minor dimension of said at least one fine feature element is in the range of from 90 nm up to and including 20 microns.

14. The method of claim 7, wherein a core of the TLCP mesogens in said body have an isotropic orientation state compared to that of said structural feature.

15. The method of claim 7, wherein for the article, all of the TLCP mesogens in the body have an isotropic orientation state compared to that of said fine feature element.

16. The method of claim 7, wherein for the article, the TLCP mesogens in said body are in a flow tumbled state.

17. The method of claim 7, wherein for the article, said 3-dimensional structural feature is a cube, rib, ridge, solid needle, hollow needle, pin, fin, gear, channel, socket, bobbin, pump, chip carrier or switch.

18. The method of claim 17, wherein for the article, said fine feature element comprises a leading edge or tip of said 3-dimensional structural feature.

19. The method of claim 18, wherein for the article, said fine feature element is a tip of said hollow needle, a tip of said solid needle, a tip of said pin, a gear tooth of said gear, opposite edges defining an opening of said channel, or a bore of said hollow needle.

20. The method of claim 1, wherein the mesogens of the TLCP solidified in the at least one fine feature chamber are molecularly aligned, relative to the flow direction of the moving molten composition filling the at least one fine feature chamber, by an anisotropy factor in the range of from greater than 0.6 up to 1.0.

* * * * *